US011499841B2

(12) United States Patent
Houfburg et al.

(10) Patent No.: US 11,499,841 B2
(45) Date of Patent: Nov. 15, 2022

(54) ENERGY-EFFICIENT POSITION DETERMINING WITH MULTIPLE SENSORS

(71) Applicant: Osprey Medical Inc., Minnetonka, MN (US)

(72) Inventors: Rodney L. Houfburg, Prior Lake, MN (US); Dale Brady, New Brighton, MN (US); Steven John Rathjen, South Lake Tahoe, CA (US); Alexander Dietz, Minneapolis, MN (US)

(73) Assignee: Osprey Medical, Inc., Minnetonka, MN (US)

( * ) Notice: Subject to any disclaimer, the term of this patent is extended or adjusted under 35 U.S.C. 154(b) by 75 days.

(21) Appl. No.: 16/845,414

(22) Filed: Apr. 10, 2020

(65) Prior Publication Data

US 2020/0326209 A1 Oct. 15, 2020

Related U.S. Application Data

(60) Provisional application No. 62/832,963, filed on Apr. 12, 2019.

(51) Int. Cl.
*G01D 5/14* (2006.01)
*G01D 5/20* (2006.01)
(Continued)

(52) U.S. Cl.
CPC ............... *G01D 5/145* (2013.01); *G01D 5/20* (2013.01); *G01D 5/241* (2013.01); *G01D 5/26* (2013.01)

(58) Field of Classification Search
CPC .......... G01D 5/145; G01D 5/20; G01D 5/241; G01D 5/26; A61M 5/31568; A61M 5/315;
(Continued)

(56) References Cited

U.S. PATENT DOCUMENTS 3,469,578 A 9/1969 Bierman
3,543,759 A 12/1970 McWhorter
(Continued)

FOREIGN PATENT DOCUMENTS

DE 19643813 4/1998
EP 523343 1/1993
(Continued)

OTHER PUBLICATIONS

Cigarroa, et al., "Dosing of Contrast Material to Prevent Nephropathy in Patients with Renal Disease", Am. Jour. of Med., Jun. 1989, pp. 649-652.
(Continued)

*Primary Examiner* — Akm Zakaria
(74) *Attorney, Agent, or Firm* — Merchant & Gould P.C.

(57) ABSTRACT

An example position determining apparatus, includes a power source, position sensors, and a controller. The position sensors are each selectively powered by the power source and configured to provide a respective sensor reading indicating a proximity of a tracked object. The controller is configured to receive respective sensor readings from the position sensors and identify a position sensor that provided an extremum sensor reading. Based on the sensor readings, the controller selectively cause powering of certain position sensors and prevents powering of other position sensors. The position sensor that provided the extremum sensor reading is one of the powered position sensors. A position output based on the sensor readings is also provided.

19 Claims, 13 Drawing Sheets

(51) Int. Cl.
*G01D 5/241* (2006.01)
*G01D 5/26* (2006.01)

(58) Field of Classification Search
CPC .... A61M 5/1452; A61M 5/178; A61M 5/172; A61M 2205/3389; A61M 2205/3317; A61M 2205/8212; A61M 2205/50
See application file for complete search history.

(56) References Cited

U.S. PATENT DOCUMENTS 3,556,122 A 1/1971 Laerdal
3,572,375 A 3/1971 Rosenberg
3,626,978 A 12/1971 Hoekstra
3,633,613 A 1/1972 Julow
3,661,174 A 5/1972 Cripe
3,695,575 A 10/1972 Hauser
3,818,929 A 6/1974 Braukmann
3,905,382 A 9/1975 Waterston
3,941,149 A 3/1976 Mittleman
3,958,573 A 5/1976 Wiley
3,985,141 A 10/1976 Stanley et al.
4,000,741 A 1/1977 Binard et al.
4,006,736 A 2/1977 Kranys et al.
4,030,497 A 6/1977 Binard et al.
4,044,793 A 8/1977 Krueger et al.
4,074,714 A 2/1978 Binard et al.
4,077,405 A 3/1978 Haerten et al.
4,084,606 A 4/1978 Mittleman
4,136,708 A 1/1979 Cosentino et al.
4,142,525 A 3/1979 Binard et al.
4,147,170 A 4/1979 Taylor
4,240,430 A 12/1980 Binard et al.
4,289,006 A 9/1981 Hallengren
4,318,400 A 3/1982 Peery et al.
4,329,985 A 5/1982 Bonchek
4,381,006 A 4/1983 Genese
4,392,847 A 7/1983 Whitney et al.
4,403,988 A 9/1983 Binard et al.
4,457,751 A 7/1984 Rodler
4,481,008 A 11/1984 Kurtz
4,501,291 A 2/1985 Siegrist
4,502,502 A 3/1985 Krug
550,747 A 11/1985 Woodworth et al.
4,602,700 A 7/1986 Szabo
4,655,746 A 4/1987 Daniels et al.
4,671,786 A 6/1987 Krug
4,744,786 A 5/1988 Hooven
4,755,172 A 7/1988 Baldwin
4,758,223 A 7/1988 Rydell
4,795,431 A 1/1989 Walling
4,813,937 A 3/1989 Vaillancourt
4,838,857 A 6/1989 Strowe et al.
4,845,493 A 7/1989 Howard
4,867,743 A 9/1989 Vaillancourt
4,997,420 A 3/1991 LeFevre
5,059,174 A 10/1991 Vaillancourt
5,094,148 A 3/1992 Haber et al.
5,139,484 A 8/1992 Hazon et al.
5,167,631 A 12/1992 Thompson et al.
5,273,187 A 11/1993 Suzuki
5,376,785 A 12/1994 Chin et al.
5,460,609 A 10/1995 O'Donnell
5,534,691 A 7/1996 Holdaway et al.
5,556,386 A 9/1996 Todd
5,573,515 A 11/1996 Wilson et al.
5,575,767 A 11/1996 Stevens
5,662,612 A 9/1997 Niehoff
5,681,285 A 10/1997 Ford
5,685,851 A 11/1997 Murphy et al.
5,707,356 A 1/1998 Paul
5,752,940 A 5/1998 Grimard
5,785,681 A 7/1998 Indravudh
5,792,117 A 8/1998 Brown
5,799,700 A 9/1998 Teh et al.
5,800,397 A 9/1998 Wilson et al.
5,806,519 A 9/1998 Evans, III et al.
5,807,321 A 9/1998 Stoker
5,827,941 A 10/1998 Good et al.
5,840,026 A 11/1998 Uber, III et al.
5,840,071 A 11/1998 Kriesel et al.
5,882,338 A 3/1999 Gray
5,882,343 A 3/1999 Wilson et al.
5,885,216 A 3/1999 Evans, III et al.
5,916,165 A 6/1999 Duchon et al.
5,954,700 A 9/1999 Kovelman
6,019,747 A 2/2000 McPhee
6,086,559 A 7/2000 Enk
6,113,578 A 9/2000 Brown
6,159,180 A 12/2000 Kriesel et al.
6,270,481 B1 8/2001 Mason
6,317,623 B1 11/2001 Griffiths et al.
6,397,098 B1 5/2002 Uber, III et al.
6,409,699 B1 6/2002 Ash
6,442,418 B1 8/2002 Evans, III et al.
6,558,125 B1 5/2003 Futterknecht
6,645,177 B1 11/2003 Shearn
6,850,792 B2 2/2005 Ohishi
6,858,020 B2 2/2005 Rusnak
6,866,654 B2 3/2005 Callan et al.
6,889,074 B2 5/2005 Uber, III et al.
6,901,283 B2 5/2005 Evans, III et al.
6,966,893 B2 11/2005 Holtby et al.
6,969,353 B2 11/2005 Brock-Fisher et al.
6,970,735 B2 11/2005 Uber, III et al.
7,022,107 B1 4/2006 Christensen et al.
7,065,395 B2 6/2006 Lienard et al.
7,094,216 B2 8/2006 Trombley, III et al.
7,255,684 B2 8/2007 Zubry
7,270,648 B2 9/2007 Kazemzadeh
7,326,186 B2 2/2008 Trombley, III et al.
7,470,253 B2 12/2008 Kriesel et al.
7,516,760 B2 4/2009 Weber
7,559,483 B2 7/2009 Hickle
7,611,503 B2 11/2009 Spohn et al.
7,618,412 B2 11/2009 Chernack
7,678,070 B2 3/2010 Kumar et al.
7,766,885 B2 8/2010 Olsen
7,815,604 B2 10/2010 Massengale et al.
7,854,726 B2 12/2010 Fago et al.
7,925,330 B2 4/2011 Kalafut et al.
7,927,305 B2 4/2011 Yribarren et al.
7,951,129 B2 5/2011 Chinchoy
7,955,301 B1 6/2011 McKay
8,075,490 B2 12/2011 Lofgren et al.
8,147,448 B2 4/2012 Sundar et al.
8,172,790 B2 5/2012 Hunter et al.
8,197,443 B2 6/2012 Sundar et al.
8,197,444 B1 6/2012 Bazargan et al.
8,208,994 B2 6/2012 Niethammer
8,257,310 B2 9/2012 Donovan et al.
8,295,914 B2 10/2012 Kalafut et al.
8,303,547 B2 11/2012 Brown
8,323,267 B2 12/2012 Haase
8,328,758 B2 12/2012 Childers et al.
9,320,846 B2 4/2016 Burns et al.
9,999,718 B2 6/2018 Brady et al.
10,413,677 B2 9/2019 Houfburg et al.
2001/0039396 A1 11/2001 Kriesel et al.
2002/0087125 A1 7/2002 Pokorney
2002/0128611 A1 9/2002 Kandalaft
2002/0198496 A1 12/2002 Duchon
2003/0055380 A1 3/2003 Flaherty
2003/0233069 A1 12/2003 Gillespie, Jr. et al.
2004/0015123 A1 1/2004 Smith
2004/0135078 A1 7/2004 Mandro et al.
2004/0138615 A1 7/2004 Lombardi
2004/0143212 A1 7/2004 Trombley et al.
2004/0178255 A1 9/2004 Eich et al.
2004/0226183 A1 11/2004 Sielemann
2005/0020983 A1 1/2005 Schreijag et al.
2005/0059931 A1 3/2005 Garrison et al.
2005/0165364 A1 7/2005 DiMatteo et al.
2005/0277912 A1 12/2005 John

(56) References Cited

U.S. PATENT DOCUMENTS

| | | | |
|---|---|---|---|
| 2006/0178632 A1 | 8/2006 | Trombley, III et al. | |
| 2007/0060820 A1 | 3/2007 | Lofgren et al. | |
| 2007/0062250 A1 | 3/2007 | Krulevitch et al. | |
| 2007/0066939 A1 | 3/2007 | Krulevitch et al. | |
| 2007/0093752 A1 | 4/2007 | Zhao et al. | |
| 2007/0161970 A1 | 7/2007 | Spohn et al. | |
| 2008/0004507 A1 | 1/2008 | Williams, Jr. et al. | |
| 2008/0147007 A1 | 6/2008 | Freyman et al. | |
| 2008/0154187 A1 | 6/2008 | Krulevitch et al. | |
| 2008/0164970 A1 | 7/2008 | Malzahn | |
| 2008/0287865 A1 | 11/2008 | Nielsen et al. | |
| 2008/0312536 A1 | 12/2008 | Dala-Krishna | |
| 2009/0234231 A1 | 9/2009 | Knight et al. | |
| 2010/0004571 A1 | 1/2010 | Nilsson et al. | |
| 2010/0016796 A1 | 1/2010 | Derichs | |
| 2010/0114064 A1 | 5/2010 | Kalafut et al. | |
| 2010/0152675 A1 | 6/2010 | McClintock | |
| 2010/0211003 A1 | 8/2010 | Sundar et al. | |
| 2010/0274180 A1 | 10/2010 | Donovan et al. | |
| 2011/0092828 A1 | 4/2011 | Spohn et al. | |
| 2012/0024987 A1 | 2/2012 | Naegele Nacken | |
| 2012/0036937 A1 | 2/2012 | Sprenger et al. | |
| 2012/0041427 A1 | 2/2012 | Caffey et al. | |
| 2012/0116217 A1 | 5/2012 | Lee-Sepsick et al. | |
| 2012/0277661 A1 | 11/2012 | Bernard et al. | |
| 2012/0277667 A1 | 11/2012 | Yodat et al. | |
| 2012/0283186 A1 | 11/2012 | Adams | |
| 2012/0302950 A1 | 11/2012 | Landsman et al. | |
| 2012/0316460 A1 | 12/2012 | Stout | |
| 2013/0261729 A1 | 10/2013 | Gillick et al. | |
| 2014/0066860 A1 | 3/2014 | Houfburg et al. | |
| 2014/0066891 A1 | 3/2014 | Burns et al. | |
| 2014/0163339 A1 | 6/2014 | Goldstein et al. | |
| 2014/0288422 A1 | 9/2014 | Brady et al. | |
| 2015/0202361 A1 | 7/2015 | Burns et al. | |
| 2015/0202386 A1 | 7/2015 | Brady et al. | |
| 2016/0213834 A1 | 7/2016 | Brady et al. | |
| 2018/0211562 A1* | 7/2018 | Rios | A61M 5/1456 |
| 2018/0272072 A1* | 9/2018 | Radmer | A61M 5/3155 |
| 2018/0318495 A1 | 11/2018 | Brady et al. | |
| 2019/0030256 A1 | 1/2019 | Brady | |
| 2020/0330691 A1* | 10/2020 | Shekalim | G01F 11/006 |

FOREIGN PATENT DOCUMENTS

| | | |
|---|---|---|
| EP | 1930603 | 6/2008 |
| JP | S62-184302 | 8/1987 |
| JP | H06-296690 | 10/1994 |
| JP | H09-506288 | 6/1997 |
| JP | 2005-523397 A | 8/2005 |
| JP | 2005-533568 A | 11/2005 |
| JP | 2007-175444 A | 7/2007 |
| WO | 84/01718 | 5/1984 |
| WO | 89/03230 | 4/1989 |
| WO | 96/11024 | 4/1996 |
| WO | 98/17974 | 4/1998 |
| WO | 02/064196 | 8/2002 |
| WO | 02/098493 | 12/2002 |
| WO | 2004/009163 | 1/2004 |
| WO | 2005/068848 | 7/2005 |
| WO | 2009/039203 | 3/2009 |
| WO | 2009/065153 | 5/2009 |
| WO | 2012/167720 | 12/2012 |
| WO | 2013/177135 | 11/2013 |
| WO | 2014/035647 | 3/2014 |
| WO | 2016/040949 | 3/2016 |

OTHER PUBLICATIONS

Davies, Justin E. et al., "Evidence of a Dominant Backward-Propagating 'Suction' Wave Responsible for Diastolic Coronary Filling in Humans, Attenuated in Left Ventricular Hypertrophy" (Circulation. 2006;113:1768-1778).

Gurm, H. et al., "Renal-Function-Based Contrast Dosing to Define Safe Limits of Radiographic Contrast Media in Patients Undergoing Percutaneous Coronary Interventions", Journal of the American College of Cardiology, 58(9): 907-914 (2011).

PCT International Search Report and Written Opinion in International Application PCT/US2016/025671, dated Jul. 26, 2016, 16 pgs.

PCT International Search Report and Written Opinion in International Application PCT/US2013/054510, dated Dec. 4, 2013, 16 pgs.

PCT International Search Report and Written Opinion in International Application PCT/US2014/052319, dated Feb. 5, 2015, 14 pgs.

PCT International Search Report and Written Opinion in International Application PCT/US2015/021294, dated Jun. 19, 2015, 13 pgs.

PCT International Search Report and Written Opinion in International Application PCT/US2016/025302, dated Jul. 20, 2016, 13 pgs.

PCT International Search Report and Written Opinion in International Application PCT/US2018/040514, dated Sep. 12, 2018, 18 pgs.

PCT International Search Report and Written Opinion in International Application PCT/US2020/027670, dated Jun. 30, 2020, 15 pgs.

PCT International Preliminary Report on Patentabilliy in Application PCT/US2020/027670, dated Oct. 21, 2021, 10 pages.

* cited by examiner

ENERGY-EFFICIENT POSITION DETERMINING WITH MULTIPLE SENSORS

CROSS REFERENCE TO RELATED APPLICATIONS

This application claims priority to U.S. Provisional Patent Application No. 62/832,963, which was filed Apr. 12, 2019, and which is entitled "ENERGY-EFFICIENT POSITION DETERMINING WITH MULTIPLE SENSORS" and which is hereby incorporated by reference for any and all purposes.

This application is related to U.S. patent application Ser. No. 15/089,061, now U.S. Pat. No. 11,2191719, which is entitled "VOLUME MONITORING SYSTEMS", published as US 2016/0213834, was filed Apr. 1, 2016, and is hereby incorporated by reference in its entirety for any and all purposes. This application is further related to U.S. patent application Ser. No. 16/024,768, now U.S. Pat. No. 11,116, 892, which is entitled "MEDIUM INJECTION DIVERSION AND MEASUREMENT", published as US 2018/0318495, was filed Jun. 30, 2018, and is hereby incorporated by reference in its entirety for any and all purposes.

INTRODUCTION

This disclosure pertains to systems, devices, and methods for energy-efficient sensor use. More specifically, the technology disclosed herein is relevant to determining a position of a tracked object in an energy-efficient manner. The tracked object can be a portion of a plunger and the resulting position information can be used to modulate or assess the delivery of media (a variety of fluidal materials that may include, at least in part, a substance used in the performance of a diagnostic, therapeutic or/and prophylactic medical procedure) to a vessel, vascular bed, organ, and/or other corporeal structures so as to optimize the delivery of media to the intended site, while reducing inadvertent or excessive introduction of the media to other vessels, vascular beds, organs, or other structures, including systemic introduction.

Energy-efficiency in determining a position of a plunger is especially useful in delivery of diagnostic or therapeutic materials during long medical procedures. Some types of procedures can last several hours, which can require changing of batteries or the manual powering-off of entire devices. While larger batteries can be used, doing so can add considerable bulk and unwieldiness to a device. Further, energy-efficiency improvements contribute to eco-friendliness of a device. Non-limiting examples of the devices that can benefit from the technologies disclosed herein are shown and described in FIGS. 1-5, which are described in more detail in the detailed description below.

BACKGROUND

The versions of the DYEVERT MODULE and the SMART-SYRINGE produced by OSPREY MEDICAL, INC. since approximately February 2018 include Hall Effect sensors to track plunger position and include a power saving feature. In particular, the sensor boards and associated firmware of these products include configurations to conserve battery life of the product by placing the product in a power savings mode when a plunger of the device is in either the completely empty or completely full position. In particular, the end sensors of an array of Hall Effect sensors remain powered on while the middle sensors are all powered off together when the plunger is positioned at either end.

FIG. 6 illustrates a partial view of an example sensor board which may be used in products such as the DYEVERT MODULE and/or the SMART-SYRINGE, identified above. As illustrated, the sensors at each end of the array of sensors are configured to always remain powered on to detect movement at all times when the device is powered. The middle nine sensors are all powered from the same controlled source and can only all be powered on, or all powered be off. A controller detects a magnet positioned at either end of the sensor array by comparing the end sensor values with a constant threshold. When the magnet is detected at either end, the middle sensors are all powered off to conserve power. Once the end sensor values drop below the constant threshold (e.g., because the plunger is moved towards the middle), the middle sensors are all powered on to detect position along the entire length of the sensor array. Periodic auditing of the magnet position is conducted while the middle sensors are powered off by temporarily powering on the middle sensors to confirm magnet position. All sensors are powered on when the device first starts until a magnet position is determined, then normal power savings management continues as described above. This configuration may provide up to an approximately 50% boost to battery savings over configurations that utilize sensors which are powered on all of the time.

SUMMARY

While the implementation described in relation to FIG. 6 provided improved energy efficiency over devices lacking such a feature, additional significant improvements are possible as described herein.

In one aspect, there is a method comprising: receiving sensor readings from a plurality of plunger position sensor sets relating to a proximity of tracked object, wherein each of plurality of plunger position sensor sets includes one or more plunger position sensors; identifying an extremum sensor reading from the sensor readings, the extremum sensor reading indicating the tracked object is nearest to an extremum-reading sensor set of the plurality of plunger position sensor sets that corresponds to the extremum sensor reading; powering, from a power source, the extremum-reading sensor set; powering, from the power source, a first adjacent sensor set, wherein the first adjacent sensor set is a sensor set of the plurality of plunger position sensor sets that is adjacent to the extremum-reading sensor set; and, preventing one or more additional sensor sets from receiving power from the power source.

In examples, the method can further include powering a second adjacent sensor set that is adjacent to the extremum-reading sensor set. The one or more additional sensor sets of the device, which in this example do not include the second adjacent sensor set, may not be powered. In another example, the first adjacent sensor set may be distal to the extremum-reading sensor set. In another example, the second adjacent sensor set may be proximal to the extremum-reading sensor set. In another example, the plurality of plunger position sensor sets may comprise a Hall Effect sensor, a light sensor, an inductive sensor, capacitive touch sensor, magnetic potentiometer position sensor, or other similar sensing elements. In another example, the one or more additional sensor sets may include all plunger position sensor sets other than the first adjacent sensor set and the extremum reading sensor. In another example, the one or more additional sensor sets may include all plunger position sensor sets other than the first adjacent sensor set, the second adjacent sensor set, and the extremum-reading sensor set. In another example, the method may further include providing a position output corresponding to a position of a tracked object using the sensor readings. In another example, the tracked object may be a plunger of a syringe. In another example, the method may further include (as an example, during an initialization process of the device) powering all plunger position sensor sets of the plurality of plunger position sensor sets. In another example, the method may include powering on all sensor sets of the plurality of plunger position sensor sets if an extremum sensor reading fails to satisfy a threshold (e.g., the sensors have "lost" the position of the magnet).

In another aspect, an apparatus may include: a syringe housing; a magnet fixed proximate the syringe housing; a plunger slidably received within the syringe housing between a first position and a second position. The plunger may include a plurality of plunger position sensor sets that include a distal plunger position sensor set comprising one or more distal plunger position sensors disposed proximate a distal end of the plunger; a proximal plunger position sensor set comprising one or more proximal plunger position sensors disposed proximate a proximal end of the plunger; and one or more intermediate plunger position sensor sets each comprising one or more intermediate plunger position sensors disposed at a location between the distal plunger position sensor set and the proximal plunger position sensor set. The plunger may further include a power source and a controller. The controller may be configured to selectively, and individually, control a power state of each respective plunger position sensor set of the plurality of plunger position sensors sets from the power source.

In examples, the controller may be configured so as to selectively control the power state of each respective plunger position sensor set based on the sensor readings from the plurality of plunger position sensors. In examples, the distal plunger position sensor set may comprise a plurality of distal plunger position sensors. In examples, the controller may further be configured to selectively control a power state of the plurality of distal plunger position sensors at an entire set-level rather than an individual-sensor level. In examples, the plunger may further comprise a shift register circuit electrically coupled to the power source, the one or more distal plunger position sensors, the one or more proximal plunger position sensors, and the one or more intermediate plunger position sensors, such that the shift register circuit is configured to control the power state of the one or more distal plunger position sensors, the one or more proximal plunger position sensors, and the one or more intermediate plunger position sensors. In examples, the controller may be configured to selectively control a power state of each respective plunger position sensor set of the plurality of plunger position sensor sets from the power source at least in part by communicating a data signal to the shift register integrated circuit. In examples, the one or more distal plunger position sensors may comprise a Hall Effect sensor, a light sensor, an inductive sensor, capacitive touch sensor, magnetic potentiometer position sensor, or other similar sensing elements.

In another aspect, there is an energy-efficient position determining apparatus that may include: a power source; a plurality of position sensors (where each of the position sensors being selectively powered by the power source and configured to provide a respective sensor reading indicating a proximity of a tracked object); and a controller. The controller may be configured to: receive the respective sensor readings of the plurality of position sensors based on the respective sensor readings; cause powering of a first group of sensors of the plurality of sensors and prevent powering of a second group of sensors of the plurality of sensors; and, provide a position output based on the respective sensor readings of the first group of sensors. The first group of position sensors may include an extremum-value position sensor identified as providing an extremum respective sensor reading. In an example, the first group of position sensors may further include a first adjacent sensor adjacent the extremum-value position sensor. In an example, the first group of position sensors may further include a second adjacent sensor adjacent the extremum-value position sensor. In an example, the power source may be an alkaline battery. In an example, the energy-efficient positioning determining apparatus may further include a shift register circuit electrically coupled to the power source, the controller, and the plurality of position sensors. The controller may be further configured to cause and prevent the powering of position sensors by providing a data signal to the shift register circuit.

This summary is provided to introduce a selection of concepts in a simplified form that are further described below in the Detailed Description. This summary is not intended to identify key features or essential features of the claimed subject matter, is not intended to describe each disclosed embodiment or every implementation of the claimed subject matter, and is not intended to be used as an aid in determining the scope of the claimed subject matter. Many other novel advantages, features, and relationships will become apparent as this description proceeds. The figures and the description that follow more particularly exemplify illustrative embodiments.

BRIEF DESCRIPTION OF THE DRAWINGS

There are shown in the drawings, embodiments which are presently preferred, it being understood, however, that the technology is not limited to the precise arrangements and instrumentalities shown.

DETAILED DESCRIPTION

Systems, methods, and apparatuses that provide position determining capabilities are described herein. In particular, techniques disclosed herein can have improved energy efficiency over prior techniques. For example, the power saving strategy described in the background required the tracked object (e.g., a magnet) to be "parked" at an end of a device to realize any power savings. By contrast, techniques described herein are relevant to providing power savings throughout an entire range of tracked object travel along an array of sensors.

Generally, position calculations for a tracked object may use, at most, three sensors: a center sensor and up to two adjacent sensors. The center sensor may be a sensor providing extremum values (e.g., maximum or minimum values) that indicate to a controller that the magnet is closest to the center sensor. The controller may then use the two side sensor values to fine-tune the position calculation. Fewer sensors can be used when, for example, the would-be center sensor is located at an end of the sensor array. In that case, the center sensor and the single adjacent sensor may be used to determine position.

After the position is determined, a power saving feature can be activated such that only the sensor groups that contain the sensors needed for the calculation (e.g., the center sensor and the two side sensors) are powered on, all other sensors are powered off. When a position determining apparatus is first powered on, all sensors can be powered until the position of the tracked object is determined. Once found, the position of the tracked object may be tracked as the tracked object moves, and sets of sensors are powered on and off as needed. If the position of the tracked object is lost (e.g., as determined by all sensors dropping below a fail-safe threshold), then all sensors may be powered back on until the position is determined. Additional details regarding power saving techniques are described herein. The techniques described herein are relevant to a wide variety of technologies including monitoring syringes, such as the ones described in FIGS. 1-5.

Figure 1:
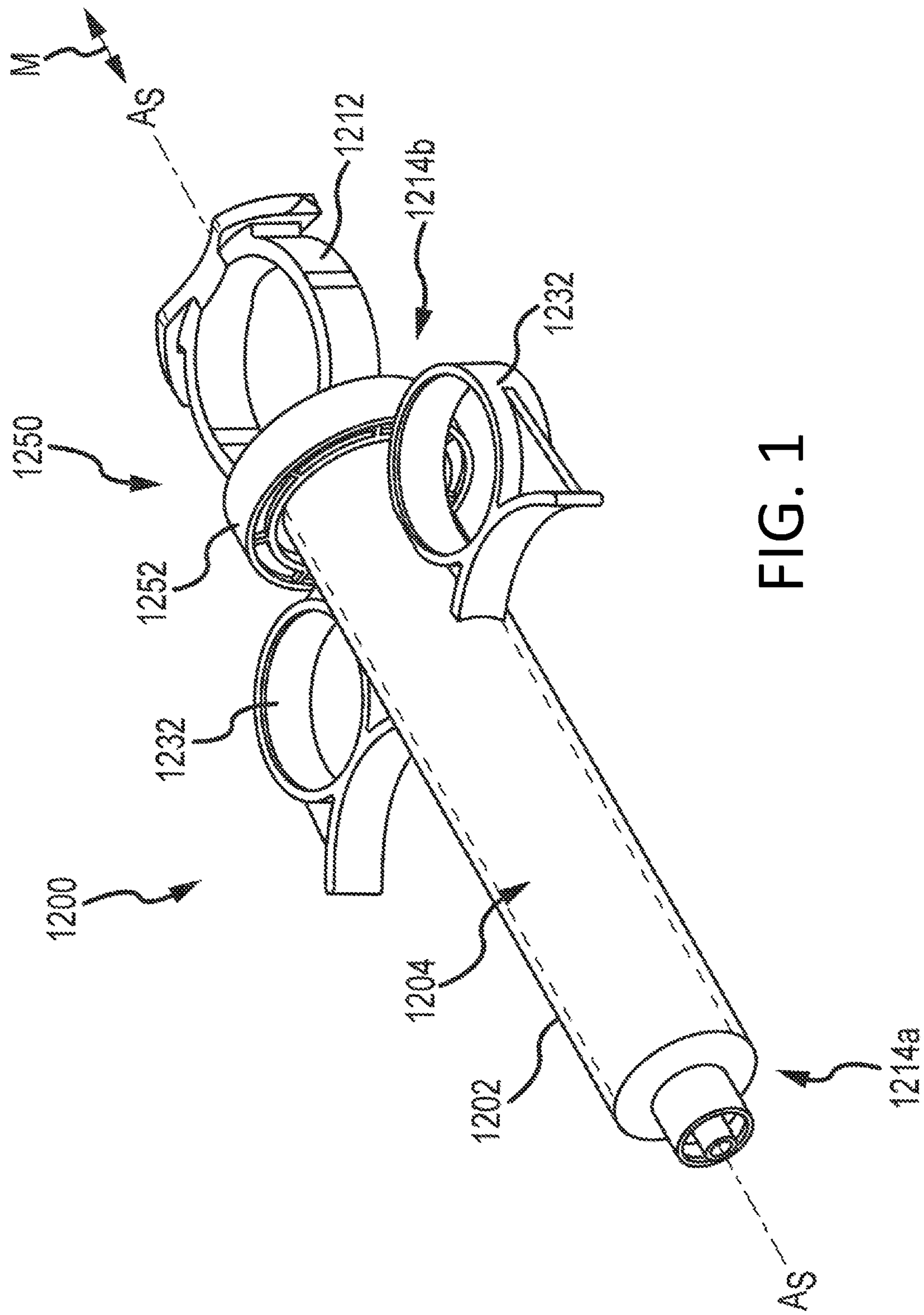
FIG. 1 depicts a perspective view of an embodiment of a monitoring syringe having a position sensor module that can benefit from the technologies described herein.

FIG. 1 depicts a perspective view of an embodiment of a monitoring syringe 1200 utilizing a position sensor module 1250 that can benefit from the technologies described herein. The monitoring syringe 1200 includes a syringe housing 1202 defining an inner bore 1204. A plunger or piston, which is described in more detail below, is slidably received in the bore 1204. More specifically, the piston is slidably engaged with an interior surface of the bore 1204 and linear movement M of a plunger shaft within the bore 1204 moves the piston. Movement M is along the syringe axis As. A thumb ring 1212 may be utilized to push and pull the plunger along axis As, as described in more detail below. As the plunger is moved M in a direction towards the discharge end 1214*a* of the syringe housing 1202, the fluid (e.g., media) contained therein is discharged into a tube or needle (not shown) and delivered to a patient. Two finger rings or tabs 1232 may receive the fingers of a user during use. Note that throughout the description a cylindrical-type syringe housing 1202 and inner bore 1204 are described; however, it is contemplated that there may be a variety of constructions of a housing/bore 1202/1204 and plunger that provide the function as anticipated herein and the shape (including rectangular, ovular, triangular cross-section, etc.), in and of itself, should not be limiting. The monitoring syringe 1200 also includes a position sensor module 1250, described in more detail below. One component of the position sensor module 1250 is a magnet retention ring 1252, which is disposed on an outer or exterior surface of the syringe housing 1202. In the depicted embodiment, the magnetic retention ring 1252 is disposed proximate a proximal end 1214*b* of the housing 1202, but it may be disposed in other locations along the housing 1202.

Figure 2:
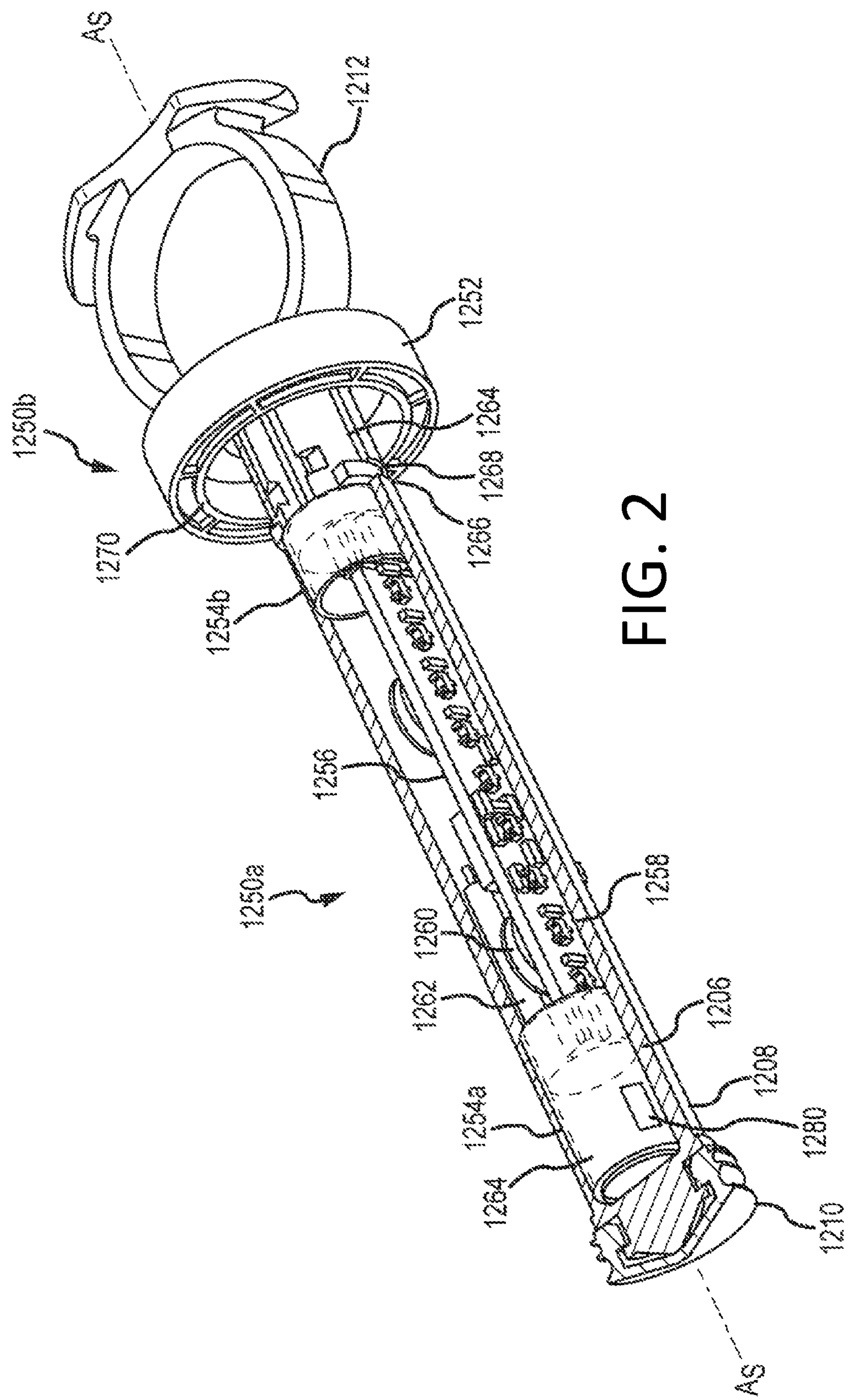
FIG. 2 depicts a partial perspective sectional view of the monitoring syringe of FIG. 1, depicting the position sensor module.

FIG. 2 depicts a partial perspective sectional view of the monitoring syringe 1200 of FIG. 1, depicting the position sensor module 1250. Certain components 1250*a* of the position sensor module 1250 are disposed within an inner chamber of a hollow shaft 1208 of the plunger 1206, while certain components 1250*b* are disposed on an exterior surface of the syringe housing. These various components 1250*a*, 1250*b* are described in more detail below. So-called internal components 1250*a* (i.e., internal to the plunger 1206) include retention inserts 1254*a*, 1254*b*, a base or circuit board 1256, and a plurality of position sensors 1258 disposed thereon. One or more batteries 1260 and a control switch 1262 may also be secured to the circuit board 1256. Signals from the position sensors 1258 may be first processed by the circuit board 1256, which may determine the position of the plunger 1206, the volume of media in the syringe, etc., and then send this information to an associated system via the transmitter 1280 for further analysis, display to a doctor, etc. In another embodiment, e.g., if a non-processing base is used, the signals from each position sensor 1258 may be sent directly via the transmitter 1280 to an associated system for processing.

The position sensors 1258 can take the form of any of a variety of sensors. For example, a single sensor, or multiple sensors, may be used to measure a magnetic field, material resistance, capacitance, etc. The measurements from such sensors may be utilized to determine the linear position of the plunger within the syringe. Examples of such sensors include, but not limited to, Hall Effect sensors, inductive sensors, capacitive touch sensors, magnetic potentiometer position sensors, and others.

The distal retention insert 1254*a* may be inserted into the shaft 1208 so as to be near the piston 1210. The distal retention insert 1254*a* may define a void, which may contain a wireless transmitter 1280, such as a BLUETOOTH transmitter. The transmitter 1280 may send signals from the position sensors 1258 to an associated signal processing device such as described herein. In an alternative embodiment, a cable connection such as described above, may be utilized. The proximal retention insert 1254*b* is disposed in the hollow shaft 1208 near the thumb ring 1212. Together, the distal retention insert 1254*a* and the proximal retention insert 1254*b* support, protect, and retain the circuit board 1256 within the hollow shaft 1208. These two components may be configured for a snug fit in the shaft 1208, or may include a key or other projection to engage with an opening or slot in the shaft 1208, so as to prevent rotation. The retention inserts 1254*a*, 1254*b* may be permanently fixed within the shaft 1208, although configuring the inserts 1254*a*, 1254*b* for removal may be advantageous so as to allow for replacement or repair of the circuit board 1256, batteries 1260, etc. In one embodiment, the thumb ring 1212 may include a resilient base 1264 including a plurality of projections 1266 that may be engageable with mating slots 1268 in the shaft 1208. Disengaging these projections 1266 allows for removal of the retention inserts 1254*a*, 1254*b* and other internal components. A plurality of position sensors 1258 are depicted. A greater or fewer number of sensors 1258 may be utilized in various embodiments, although a greater number of sensors 1258 may provide for more accurate determinations with regard the position of the plunger 1206. The position sensors 1258 are disposed linearly within the chamber so as to be substantially aligned with, or parallel to, the axis As.

External components 1250*b* include the magnet retention ring 1252, which holds a plurality of magnets 1270, which are arc magnets, in the depicted embodiment. In other embodiments, cube, cylindrical, or other magnets may be utilized. The positions of the magnets 1270 are fixed relative to and about the syringe housing. The arc magnets 1270 form a substantially circular magnetic field through which the shaft 1208 (and the position sensors 1258) pass when the shaft 1208 is withdrawn from or inserted into the inner bore of the syringe. The circular magnetic field enables the position sensors 1258 to detect the field, regardless of the rotational position of the plunger 1206 about the axis As. In other embodiments, the magnets 1270 may be secured directly to the syringe housing without the magnet retention ring.

Figure 3:
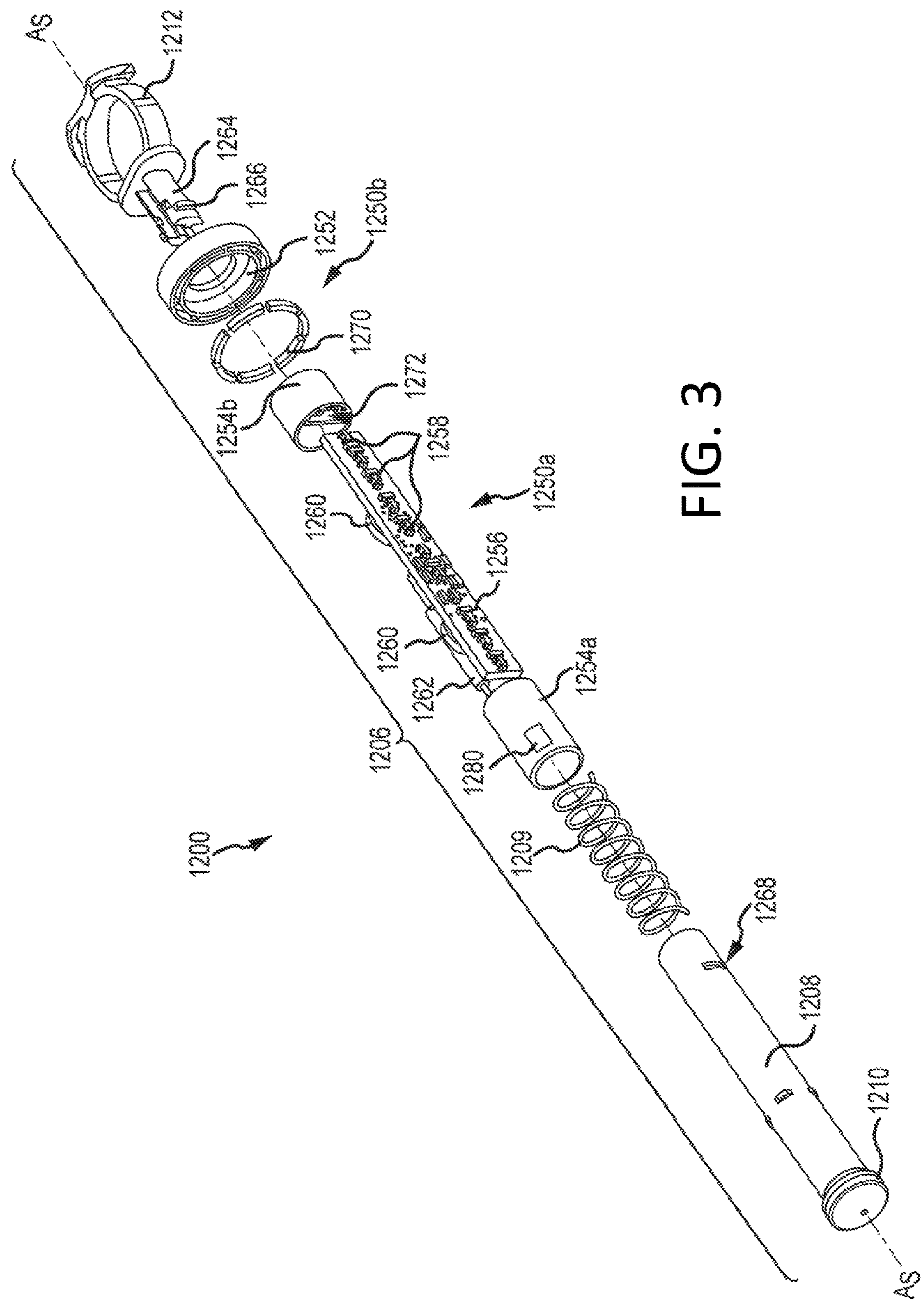
FIG. 3 depicts a partial exploded perspective view of a portion of the monitoring syringe, as seen in FIG. 2.
Figure 4:
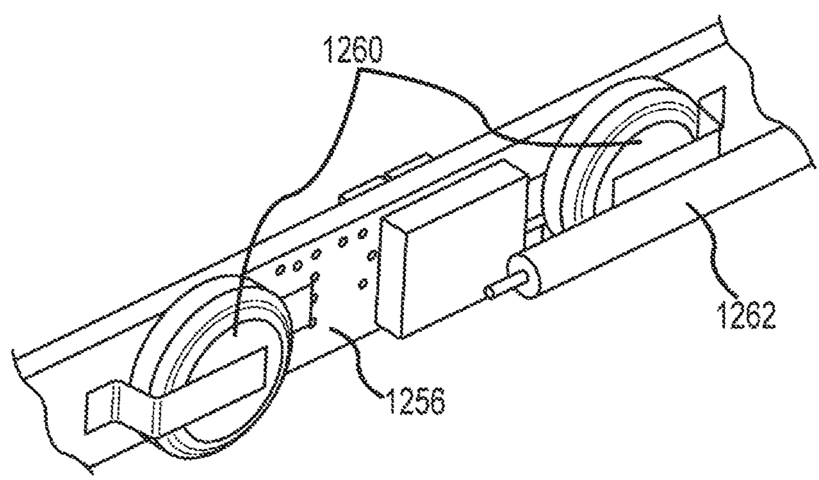
FIG. 4 depicts a partial perspective view of a Hall Effect sensor module.

FIG. 3 depicts a partial exploded perspective view of a portion of the monitoring syringe 1200, as seen in FIG. 2. More specifically, the plunger 1206, position sensor module internal components 1250*a*, and position sensor module external components 1250*b* are depicted. In general, certain of these components are described above in FIGS. 1 and 2 are not necessarily described further. In the depicted embodiment, however, both the distal retention insert 1254*a* and proximal retention insert 1254*b* include shaped recesses 1272 that are configured to receive the circuit board 1256 so as to hold that element in place. The recesses 1272 are disposed in the inserts 1254*a*, 1254*b* so as to conserve space within the hollow shaft 1208 of the plunger 1206. On a side of the circuit board 1256 opposite the position sensors 1258 are disposed a plurality of batteries 1260. This is also depicted in FIG. 4. Additionally, a switch 1262 may be disposed proximate the batteries 1260 or elsewhere within the hollow shaft 1208. The switch 1262, in certain embodiments, may be a reed switch that detects plunger movement and moves to an engaged or activated position. The switch 1262 is not required but may help preserve power when the syringe 1200 is not in use. When activated, the switch 1262 selectively connects power from the batteries 1260 to either or both of the plurality of position sensors 1258 and the wireless transmitter 1280. In other embodiments, a manually-operated switched, such as a pull tab, button, or rocker switch may be actuated by the user.

In a further embodiment of a system, the measurement components of a monitoring syringe 1200 could also be utilized to measure a volume of medium diverted by a modulator to a medium diversion reservoir (as further described in related to U.S. patent application Ser. No. 16/024,768, previously incorporated by reference herein), in systems that employ a reservoir in the introduction of contrast to a patient. Such medium diversion reservoirs, and their incorporation into related medium management and monitoring systems, are described and may be found in the referenced application. In such cases, the inner bore 1204 may form a fluid reservoir to capture medium that may diverted by a modulator away from the injection of medium to the delivery catheter. In an additional embodiment of a reservoir, the chamber may be sufficiently pressurized by a force acting upon the plunger 1206 to facilitate controlled filling, release and measurement of a medium within the chamber. The force may bias the piston 1210 into the fluid contained in the bore 1204, while the position sensors 1258 continue to detect a position of the plunger 1206. In the depicted example, to configure the monitoring syringe 1200 as a pressurized diversion reservoir, a spring 1209 may be disposed about the hollow shaft 1208 of the plunger 1206. This spring 1209 biases the piston 1210 towards the discharge end 1214*a* of the syringe housing 1202. Other spring configurations and/or biasing mechanisms may be utilized, wherein they may be generally disposed about the syringe axis As so as to provide for a balanced application of force. The configuration of this reservoir, with measurement capabilities, incorporates sensing elements assembled along the axis of the housing, and the location magnet is affixed the plunger and/or plunger shaft/piston. It is contemplated that either, or any other configuration, may be advantageously benefited by the power management embodiments described. That is to say, whether the position sensors move along a fixed sensor element position (e.g., a magnet for example), or that the sensor element (e.g., magnet, for example) passes along a set of fixed position sensors, the energy management systems described herein may be of benefit of either, or other configurations.

Figure 5:
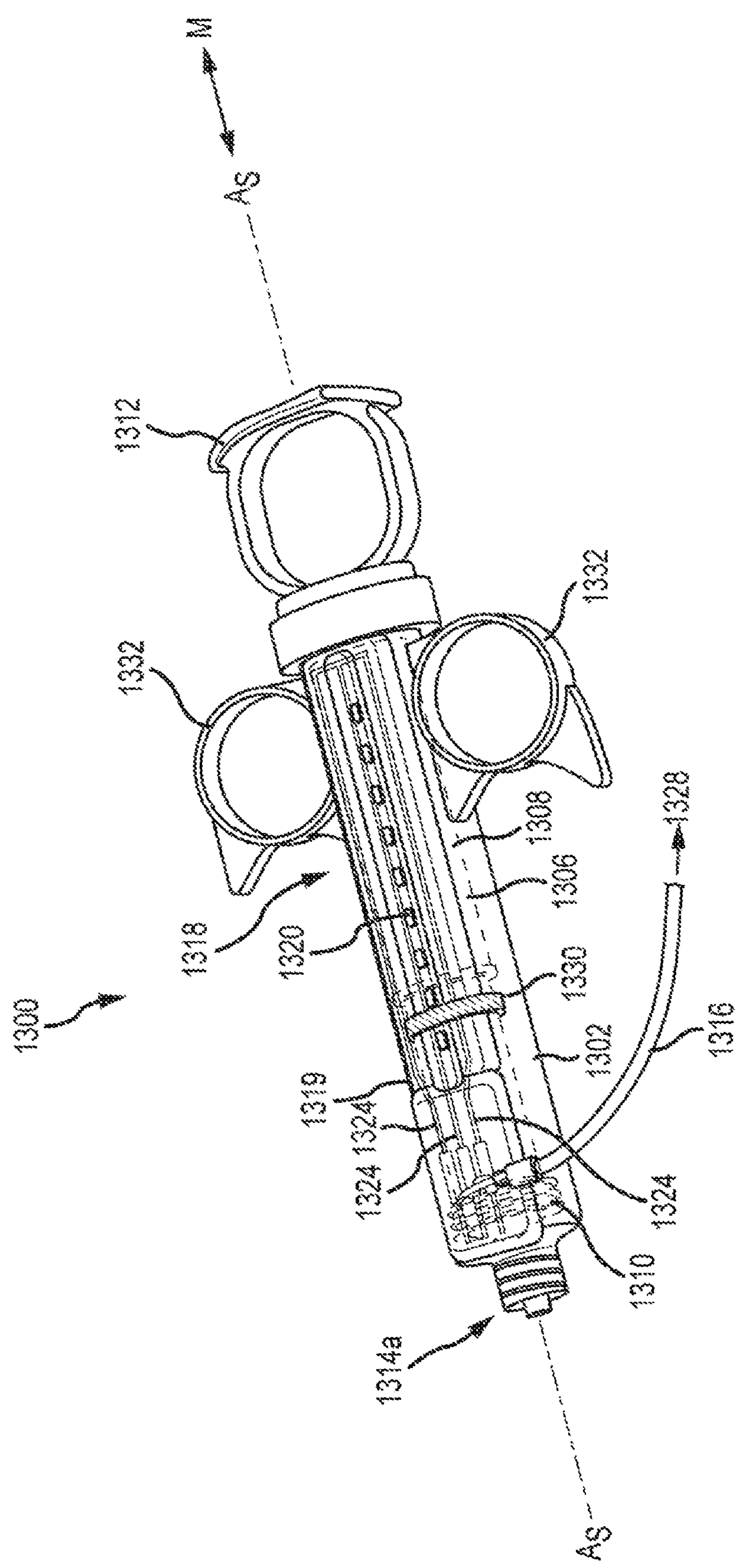
FIG. 5 depicts a perspective view of a second embodiment of a monitoring syringe having a position sensor module.

FIG. 5 depicts a perspective view of a second embodiment of a monitoring syringe 1300 utilizing a position sensor module. The monitoring syringe 1300 includes a syringe housing 1302 defining a hollow inner bore. A plunger 1306 including a shaft 1308 and a piston 1310 is slidably received in the bore. More specifically, the piston 1310 may be slidably engaged with an interior surface of the bore and linear movement M of the shaft 1308, within the bore, moves the piston 1310. Movement M is along the syringe axis As. The plunger 1306 is moved back and forth within the bore 1304 by the movement of a thumb pad, such as a thumb-ring 1312. As the plunger 1306 is moved M in a direction towards the discharge end 1314*a* of the syringe housing 1302, the fluid contained therein is discharged into a manifold assembly, tube, or needle (not shown) and delivered to a patient.

As an alternative embodiment to that depicted in FIGS. 2 and 3, a position sensor module 1318 may be secured to an exterior surface of the syringe housing 1302, rather than securement to the plunger. The position sensor module 1318 includes a Hall sensor housing 1319 that encloses a plurality of Hall sensors 1320. As described above with regard to FIGS. 1-3, a greater number of discrete Hall sensor elements may improve accuracy. One or more leads or wires 1324 extend from an end of the position sensor module 1318. A cable 1326 connects at an end 1328 to an interface unit that analyzes the output of the position sensor module 1318 and provides this information to a user of the monitoring syringe 1300, typically on a display. In other embodiments, communication may be via a radio, Bluetooth, of other wireless connection, as described herein. The displayed information may include volume of the chamber, volume remaining, volume dispensed, fluid type, flow rate, fluid pressure or temperature and/or other information, as required or desired for a particular application. As described above, the signals from the Hall sensors may first be processed by an associated circuit board then sent to an interface unit, or the discrete signals may be sent to the interface unit for processing.

In the depicted embodiment, the shaft 1308 of the plunger 1306 has one or more magnets 1330 disposed thereon or within the shaft 1308. The magnet 1330, in this case, includes a plurality of arc magnets disposed about the shaft 1308. As the plunger 1306 is slidingly moved M along the axis As, the magnet 1330 passes in front of the Hall sensors 1320 of the position sensor module 1318. The magnetic field generated by the magnet 1330 is detected by the Hall sensor 1320. The Hall sensor 1320 sends a signal to the interface unit that determines the position of the plunger 1306 within the syringe housing 1302, based on the position of the magnet 1330 as detected by an individual Hall sensor 1320. Thus, the position of the plunger 1306 can be determined. The interface may also determine the various types of information listed above, based on a known diameter and length of the bore 1304 of the syringe housing 1302. Two finger rings or tabs 1332 may receive the fingers of a user during use. A stop 1334 prevents the plunger 1306 from being pulled out of the syringe housing 1302.

Energy-Efficient Position Determining

Figure 7:
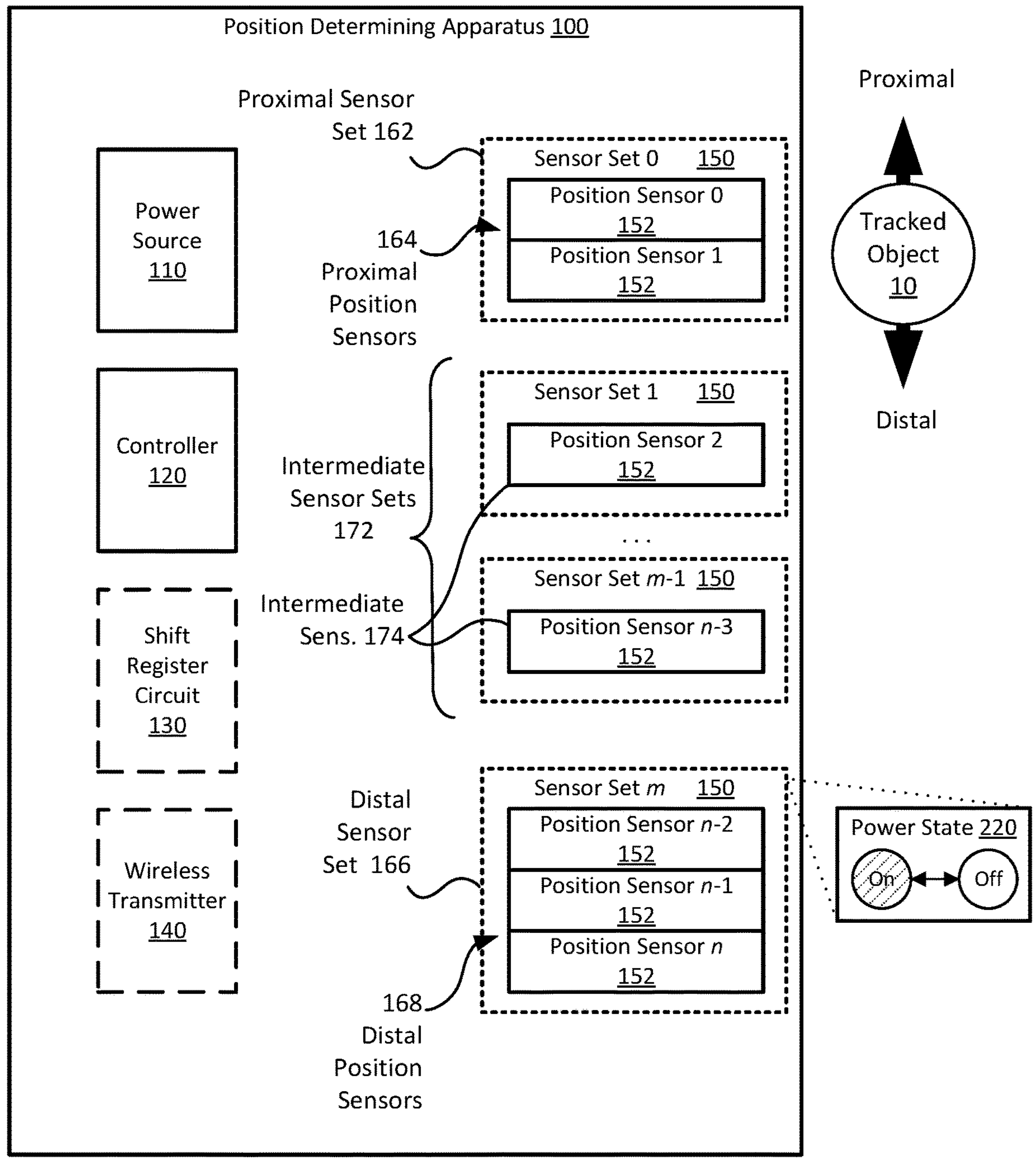
FIG. 7 illustrates an example position determining apparatus configured to determine the position of a tracked object.

FIG. 7 illustrates an example position determining apparatus 100 configured to determine a position of a tracked object 10. In examples, the position determining apparatus 100 can be a component of (e.g., operate as the position sensor module 1250) or used in conjunction with the devices discussed in FIGS. 1-4. For instance, the tracked object 10 may be the plunger 1206 of the monitoring syringe 1200 of FIG. 1.

In the example illustrated in FIG. 7, the position determining apparatus 100 may include a power source 110, a controller 120, and a plurality of sensor sets 150. In some examples, the position determining apparatus 100 may further include a shift register circuit 130. In some examples, the position determining apparatus 100 may further include a wireless transmitter 140.

The power source 110 is a source of electric power for use by one or more components of the position determining apparatus 100. In many examples, the power source 110 is a battery (e.g., the one or more batteries 1260 of FIG. 2). In examples, the power source 110 is an alkaline battery, which are advantageously considered disposable in many jurisdictions without the need for special handling. Disposability of the power source 110 can beneficially allow the entire position determining apparatus 100 to be considered disposable, which can be an important attribute compared to, for example, rechargeable or non-rechargeable lithium ion batteries. Nevertheless, in examples, the power source 110 can be a lithium-ion battery. In further examples, the power source 110 can be a port or cable for connecting the apparatus to a source of power external to the position determining apparatus 100. In still further examples, the power source 110 can be a wireless-power antenna configured to receive wireless power from another source.

The controller 120 is an electronic component of the position determining apparatus 100 that controls other components of the position determining apparatus 100. As described in many examples herein, the controller 120 can be configured to selectively activate and deactivate the sensors of the sensor sets 150 in a manner that allows for energy-efficient sensing without a significant loss in position accuracy. The controller 120 can take any of a variety of forms, such as a microcontroller or an operating environment similar to the one described in FIG. 12.

The plurality of sensor sets 150 may be each logical, or physical groups, of one or more position sensors 152. In examples, the position sensors 152 can correspond to the position sensors 1258 described above in relation to FIG. 2. Each of the position sensors 152 are selectively powered by the power source 110 and configured to provide a respective sensor reading indicating a proximity of a tracked object 10. In an example, all position sensors 152 of a single sensor set 150 are configured to share a same power state 210 without being individually addressable. The power state 210 indicates whether a sensor set 150 (and therefore the sensors 152 thereof) are powered (e.g., ON or active) or unpowered (e.g., OFF or inactive). In examples herein, the power state 210 may be controlled by the controller 120 (e.g., via the shift register circuit 130). The position sensors 152 of the single sensor set 150 can each provide a separate sensor output. The term "sensor set" can be used to refer to all position sensors 152 within a sensor set 150. For instance, the statement "turn off power to a sensor set 150" can be used to refer to turning off power to all position sensors 152 within the sensor set 150.

In the illustrated configuration, the plurality of sensor sets 150 are arranged linearly in proximal and distal directions. In this configurations, certain of the sensor sets 150 can be described by their relative positioning, such as proximal sensor set 162 having proximal position sensors 164 near a proximal end of the position determining apparatus 100, a distal sensor set 166 having one or more distal position sensors 168 near a distal end of the position determining apparatus 100, and one or more intermediate sensor sets 172 each including one or more intermediate sensors 174 located between the proximal position sensors 164 and the distal position sensors 168.

Position sensors 152 are electronic components configured to operate within the context of the position determining apparatus 100 to provide output for determining the position of a tracked object 10. In an example, a position sensor 152 is a Hall Effect sensor configured to provide output based on a magnetic field strength detected by the Hall Effect sensor that may be indicative of a proximity of a magnet to the position sensor 152. Based on the magnetic field strength, a position of the magnet relative to the position sensor can be inferred. In another example, a position sensor 152 is a light sensor configured to provide output based on an amount of light being received at the position sensor 152. The amount of light being received can be used to infer a position of a tracked object 10 (for example, a tracked object 10 could block light from reaching the position sensor 152). In still further examples, a position sensor can be an inductive sensor, a capacitive touch sensor, or another kind of sensor. Where the position sensors 152 are used to track a position of a plunger (or object associated therewith), the position sensors 152 can be referred to as "plunger position sensors" and the associated sensor sets can be referred to as "plunger position sensor sets".

The shift register circuit 130 is a circuit that behaves as a shift register. In many examples, the shift register circuit 130 is configured to receive power, serial data, and a clock signal as input and provide output at two or more (typically eight or more) output locations (typically pins) based on the input. In an example, the each output is linked to a sensor set 150 and each output is respectively usable to selectively power a respective sensor set 150. An example integrated circuit usable as the shift register circuit 130 is the 74HC164 8-bit parallel-out serial integrated circuit, such as is manufactured by TEXAS INSTRUMENTS INC.

The wireless transmitter 140 is a component of the apparatus configured to provide a wireless output. In examples, the wireless transmitter 140 is a transmitter configured to communicate according to BLUETOOTH, WI-FI, cellular, near-field, inductive, or other communication protocols or techniques.

Figure 8:
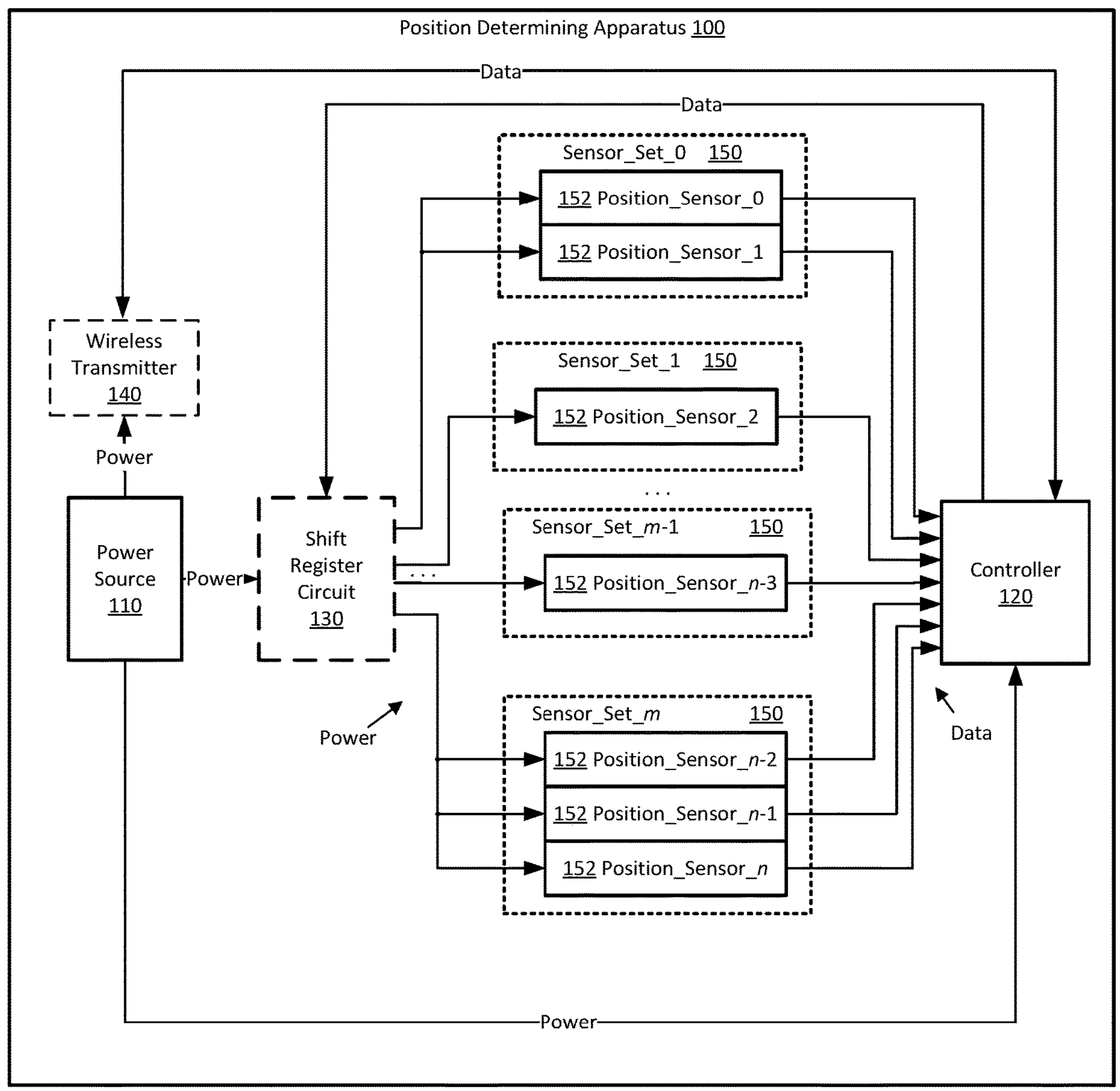
FIG. 8 illustrates an example partial configuration of components of the position determining apparatus.

FIG. 8 illustrates an example partial configuration of components of the position determining apparatus 100. In the illustrated configuration, the power source 110 is configured to provide power to the controller 120 and the position sensors 152. The illustrated configuration includes a wireless transmitter 140 powered by the power source 110.

The illustrated configuration further includes a shift register circuit 130 electrically coupled to and powered by the power source 110. The shift register circuit 130 is further electrically coupled to the sensor sets 150, such that the shift register circuit 130 is configured to control the power state of the position sensors 152 of the sensor sets 150 based on a data signal received from the controller 120.

In the illustrated example configuration, the controller 120 may be electrically connected to the position sensors 152 to receive a data signal provided by the position sensors 152. In addition, the example configuration shows that the controller 120 may be electrically connected to the wireless transmitter 140 and is configured to provide a data signal to the wireless transmitter 140. The example configuration further shows that the controller 120 is electrically connected to the shift register circuit 130 and is configured to provide a data signal to the shift register circuit to control the shift register circuit. For example, the data signal can include data controlling the power states 210 of the respective sensor sets 150 (e.g., which sensor sets 150 should be powered on or off).

In addition, the illustrated configuration shows that the shift register circuit 130 may be configured to control the power states 210 (e.g., by providing power) of the position sensors 152 at an entire-set level rather than at an individual sensor level. For example, as illustrated the Sensor_Set_0 is connected to the shift register circuit 130 such that all position sensors 152 of the sensor set 150 have the same power state 220. In other words, both Position_Sensor_0 and Position_Sensor_1 (which are part of Sensor_Set_0) have the same power state and cannot be configured to have different power states 220 from each other. This configuration can be achieved by, for example, having a single output of the shift register circuit 130 connected to multiple position sensors 152, which make up a single set.

But as can be seen in the illustrated configuration, in other configurations, some outputs of the shift register circuit 130 correspond to only a single position sensor 152 (e.g., Sensor_Set_1 and Sensor_Set_m−1). These configurations can be considered to be sensor sets 150 of size one (i.e., the sensor set 150 includes only a single position sensor 152). Thus the shift register circuit 130 is effectively able to provide power to these position sensors 152 of these sensor sets 150 at an individual-sensor level because the sensor set 150 includes only one position sensor 152.

Figure 6:
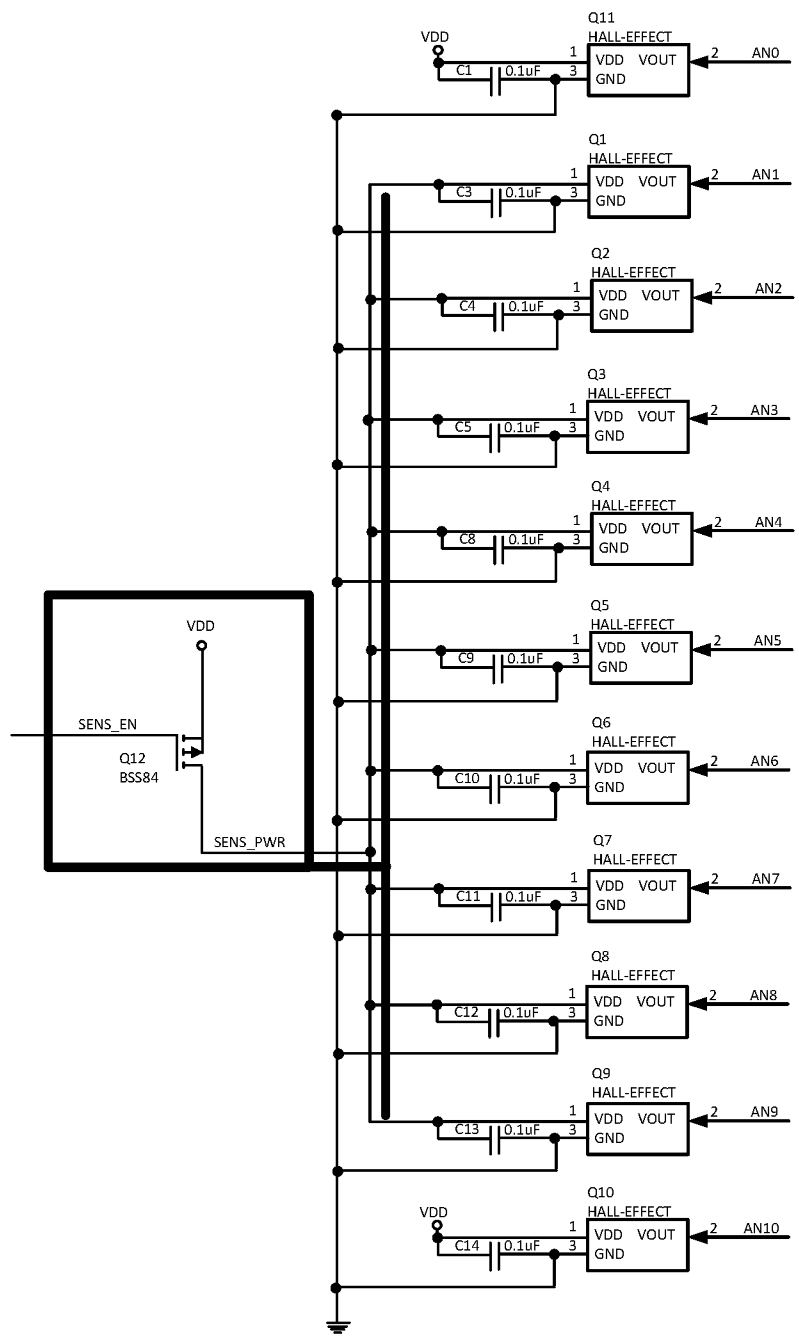
FIG. 6 illustrates a partial view of a prior art sensor board.
Figure 9:
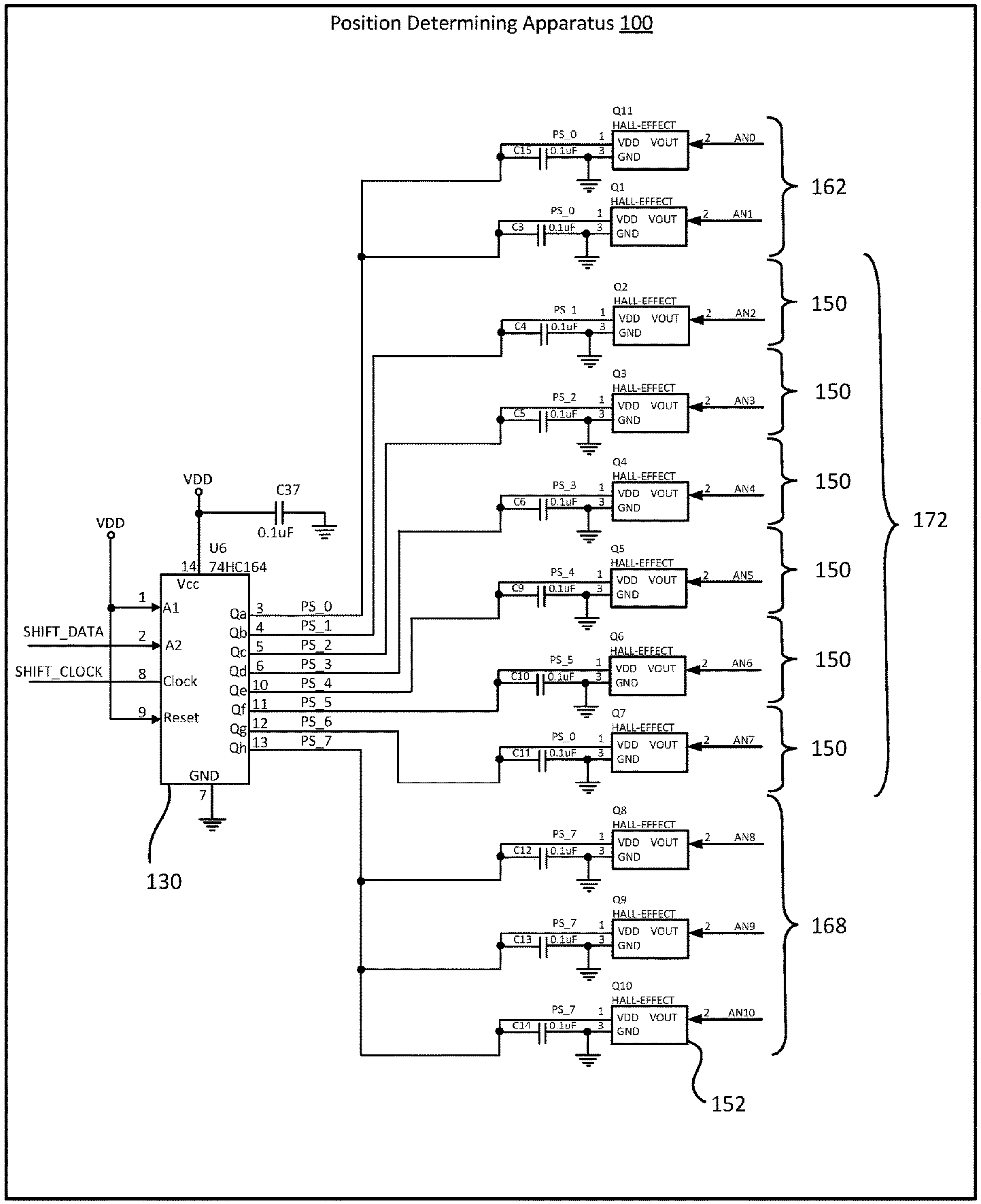
FIG. 9 illustrates an example portion of a circuit diagram of an implementation of a position determining apparatus.

FIG. 9 illustrates an example portion of a circuit diagram of an implementation of a position determining apparatus 100. In particular, the connections between the shift register circuit 130 and the sensors 152 are shown, including some additional components, such as capacitors. For example, a second control line may be made available from the controller 120 (not shown) and connect to the shift register circuit 130. In the illustrated configuration, the shift register circuit 130 is a 74HC164 integrated circuit having eight-bit output. As illustrated, end sensors were grouped together into sets to form eight separate sensor sets 150. Each sensor set 150 can have its own respective power state 220 controlled by the shift register circuit 130. As illustrated, the proximal sensor set 162 includes two position sensors 152, the distal sensor set 166 includes three position sensors 152, and each of the intermediate sensor sets includes one position sensor. The middle sensor sets may include only one sensor each. As can be seen, there are several differences between the circuit diagram of FIG. 9 and the circuit diagram of FIG. 6.

Figure 10:
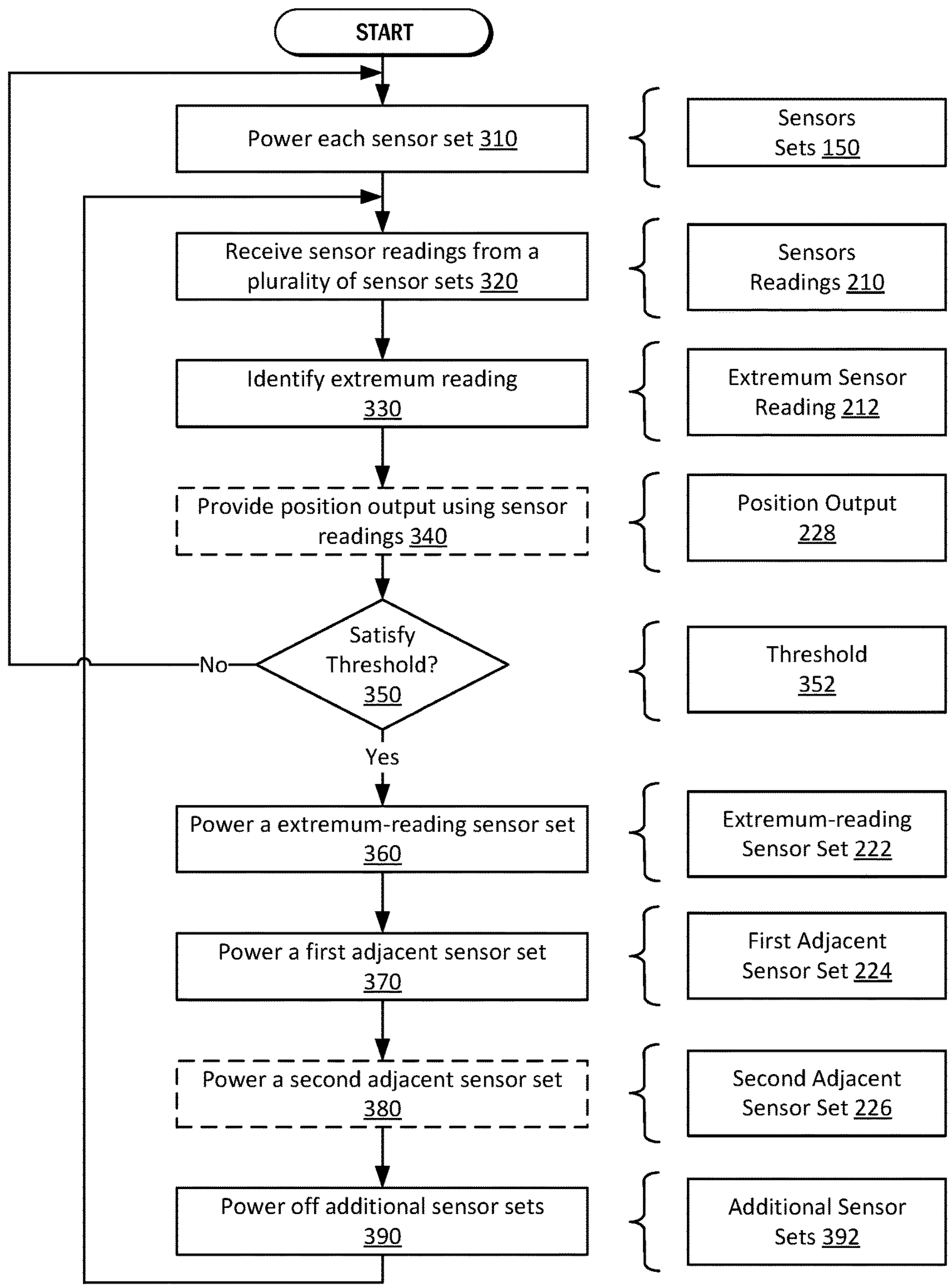
FIG. 10 illustrates an example method.

FIG. 10 illustrates an example process 300 for controlling the power states 220 of sensor sets 150. The figure further illustrates relevant aspects adjacent the method 300 operations. The method begins with operation 310. Operation 310 includes powering each sensor set 150 of the plurality of sensor sets 150. In an example, this operation can take place during an initialization process for a position determining apparatus 100 when the position determining apparatus 100 is initially powered on. Following operation 310, the flow of the process 300 moves to operation 320.

Operation 320 includes receiving sensor readings 210 from a plurality of sensor sets 150. As described above, each of plurality of sensor sets 150 can include one or more position sensors 152. Following operation 320, the flow of the process 300 moves to operation 330.

Operation 330 includes identifying an extremum sensor reading 212 from the sensor readings 210. The extremum sensor reading 212 indicates that the tracked object 10 is nearest to an extremum-reading sensor set 222 of the plurality of sensor sets 150 that corresponds to the extremum sensor reading 212. Depending on the configuration of the position determining apparatus 100, the extremum sensor reading 212 is typically a maximum sensor reading or a minimum sensor reading. For example, where the sensors sets 150 are sets of one or more Hall Effect sensors and the tracked object 10 is a magnet, the position sensors 152 of the position sensors sets 150 provide sensor readings 210 that correspond to a strength of the magnetic field. In such configurations, a sensor set 150 that provides the maximum reading of the sensor readings 210 is an extremum-reading sensor set 222 that is determined to be closer to the tracked object 10 than any other of the sensor sets 150. In other configurations, the extremum sensor reading 212 can be a minimum value, a median value, or some other value corresponding to a proximity of the tracked object. Following operation 330, the flow of the process 300 optionally moves to operation 340 or moves directly to operation 350.

Operation 340 includes providing a position output 228 corresponding to a position of a tracked object 10 using the sensor readings 210. The position output 228 can be calculated in any of a variety of ways. In some examples, the position output 228 is simply an identification of the extremum-reading sensor set 222. In other examples, the position output 228 is a value corresponding to the extremum-reading sensor set 222. For instance, the position determining apparatus 100 may store a lookup table defining predetermined positions of the sensor sets 150 or position sensors 152 thereof. Using the lookup table, a predetermined position of the extremum-reading sensor set 222 is provided as output. In other examples, the position output 228 is calculated based on two or more predetermined positions of the sensor sets 150 or the position sensors 152 thereof. For example, the position output 228 can be calculated as a weighted average of the positions of two or more extremum sensor readings with the weights corresponding to the values of the sensor readings. The position output 228 can be provided as output in a variety of ways. For instance, the position determining apparatus 100 can include an output device (e.g., a display, speaker, or a wired output) by which the position output 228 is provided. In some examples, the position output 228 is provided to the wireless transmitter 140 for wireless transmission to another device.

Operation 350 includes determining a relationship between the extremum sensor reading 212 and a threshold 352. Responsive to the extremum sensor reading 212 satisfying the threshold 352 (e.g., being greater than, greater than or equal to, equal to, less than or equal to, or less than the threshold 352 depending on how the comparison and threshold 352 are implemented), the flow of the method 300 moves to operation 360. Responsive to the extremum sensor reading 212 failing to satisfy the threshold 352, the flow of the method 300 moves to operation 310, in which all position sensor sets 150 are powered. In an example, failing to satisfy the threshold 352 indicates that the tracked object 10 is lost (e.g., the position of the tracked object 10 cannot be determined) and a corresponding error or alert is activated.

Operation 360 includes powering, from a power source 110, an extremum-reading sensor set 222. In examples, the operation 360 includes identifying a sensor set 150 of the sensor sets 150 as being the extremum-reading sensor set 222. As described above, the extremum-reading sensor set 222 is a sensor set 150 of the plurality of sensor sets 150 that corresponds to the extremum sensor reading 212. As such, identifying the extremum-reading sensor set 222 can include selecting a sensor set 150 corresponding to the extremum sensor reading 212. Following operation 360, the flow of the method 300 moves to operation 370.

Operation 370 includes powering, from the power source 110, a first adjacent sensor set 224. In examples, the operation 370 includes identifying a sensor set 150 of the sensor sets 150 as being the first adjacent sensor set 224. The first adjacent sensor set 224 is a sensor set 150 of the plurality of sensor sets 150 that is adjacent to the extremum-reading sensor set 222. As such, identifying the first adjacent sensor set 224 can include selecting a sensor set 150 as being plus or minus one position away from the extremum-reading sensor set 222. Following operation 370, the flow of the method moves to operation 390 or, optionally, operation 380.

Operation 380 includes powering a second adjacent sensor set 224. In example, the operation 380 includes identifying a sensor set 150 of the sensor sets 150 as being the second adjacent sensor set 226. The second adjacent sensor set 224 is a sensor set 150 of the plurality of sensor sets 150 that is adjacent to the extremum-reading sensor set 222. As such, identifying the first adjacent sensor set 224 can include selecting a sensor set 150 as being plus or minus one position away from the extremum-reading sensor set 222, if such a position exists and does not already identify the first adjacent sensor set 224. Following operation 380, the flow of the method moves to operation 390.

Operations 390 includes preventing one or more additional sensor sets 392 from receiving power from the power source 110. The one or more additional sensor sets 392 are sensor sets 150 that are in addition to powered sensor sets described above in relation to operation 360, operation 370, and operation 380. In an example, the additional sensor sets 392 are all sensor sets of the apparatus other than the extremum-reading sensor set 222, the first adjacent sensor set 224, and the second adjacent sensor set 226. Following operation 390, the flow of the method returns to operation 320.

While various operations of the process 300 are disclosed, these operations are described for purposes of illustrating the present methods and systems and are not intended to limit the disclosure, including to a particular sequence of steps. For example, the steps can be performed in differing order, two or more steps can be performed concurrently, additional steps can be performed, and disclosed steps can be excluded without departing from the present disclosure. As a particular example, where a shift register circuit is used to control the power states 220 of the position sensors 152, the powering on or off of particular sensor sets 150, the operations 360, 370, 380, and 390 can occur substantially concurrently. Furthermore, the present example includes a configuration that includes a shift register capable of initiating power to, say, eight outputs. As a result, powering on or off of sensor sets (versus individual sensors 152) may be accommodated to the shift register capabilities. It is also contemplated that each position sensor 152 may be accommodated with a single/individual power control to each position sensor 152. In this case, the coming and going of an extremum sensor data may initiate individual position sensors to be on or off, versus a set of two or more sensors, for example.

Figure 11:
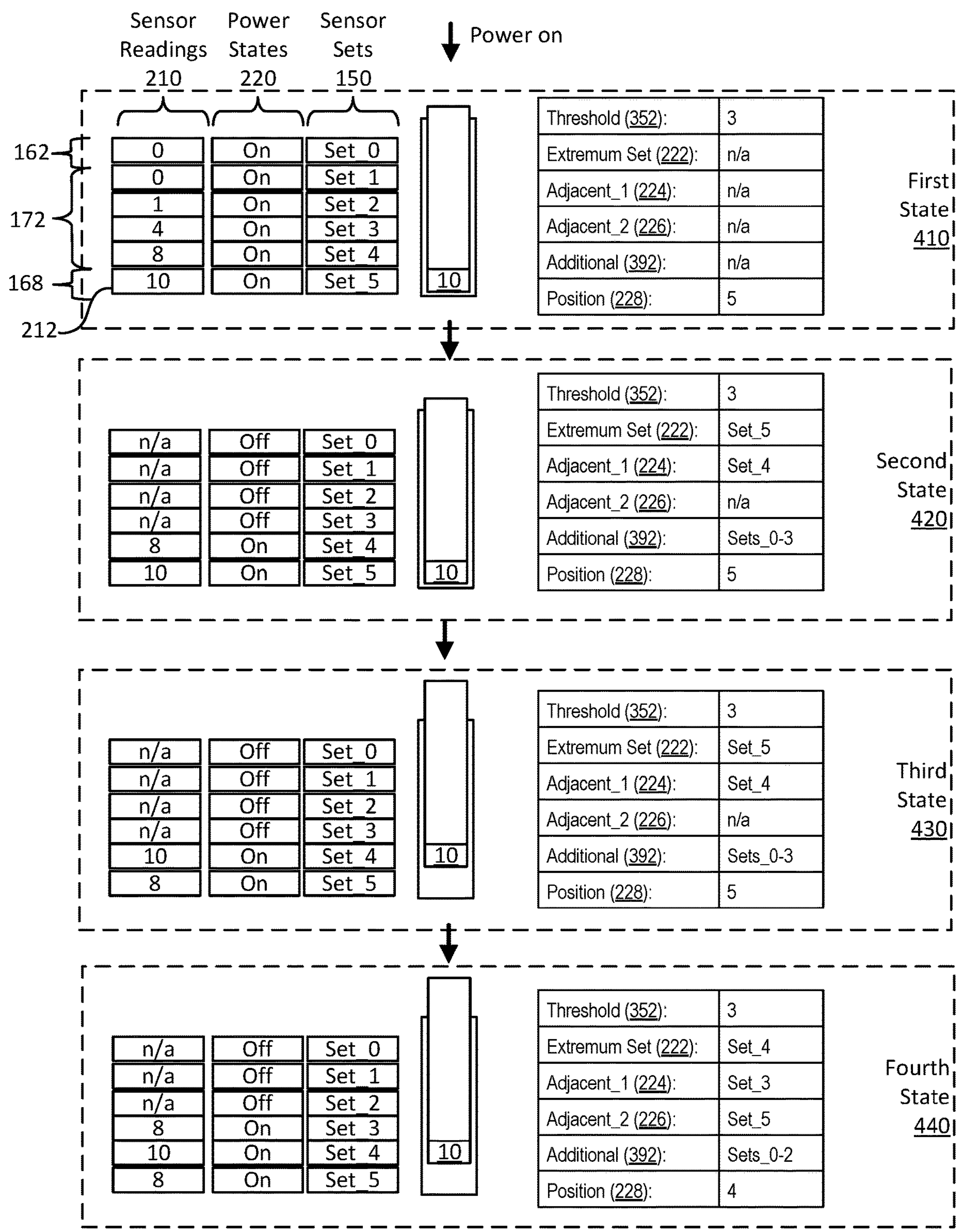
FIG. 11 illustrates an example of the use of the method to provide a position output corresponding to a position of a tracked plunger in an energy-efficient manner.

FIG. 11 illustrates an example of the use of the method 300 to provide a position output 228 corresponding to a position of a tracked object 10 (in this illustrated configuration, a tracked plunger) in an energy-efficient manner. The figure illustrates components and statuses of the position determining apparatus 100 in four different states: a first state 410, a second state 420, and a third state 430, and a fourth state 440. The figure further shows the position of the tracked object 10, the sensor sets 150, the sensor readings 210 from the sensor sets 150, and the power states 220 of each of the sensor sets 150. Additionally, the extremum-reading sensor set 222, the first adjacent set 224, the second adjacent set 226 (if any), and the position output 228 of the tracked object 10 is shown for each of the states. In the illustrated configuration, Set_5 is the distal sensor set 166, Set_0 is the proximal senor set 162, and sets Set_1-4 are the intermediate sensor sets 172.

As an example, the first state 410 shows a state after an initial power on of the position determining apparatus 100 through operation 340. As illustrated, the tracked object 10 is adjacent Set_5. As described in operation 310, all sensor sets 150 have an active (e.g., ON) power state 220. As described in operation 320, the sensor readings from the sensor sets 150 are received. The sensor reading 210 from Set_5 is the maximum value reading (or, other determinative reading of the state of the sensor data from the sensors) of all of the sensor readings 210 and is identified as the extremum/determinative reading 212 (operation 330). Based on the sensor readings 210, the position of the tracked object 10 is determined to be position 5, indicating that the tracked object 10 is proximate the predetermined position of Set_5 (operation 340). The transition from the first state 410 to the second state 420 represents the process 300 continuing through operation 390.

Moreover, as an example, a second state 420 shows a state of the position determining apparatus 100 after the first state 410 through operation 390. As described in operation 350, the extremum/determinative sensor reading 212 is compared to the threshold 352. In the example depicted, the extremum sensor reading 212 has a value of 10, which is greater than the threshold 352 having a value of 5, so the flow continues to operation 360. In the illustrated example, Set_5 is identified as the extremum-reading sensor set 222 because Set_5 has a maximum value of the sensor readings 210 and because a maximum value indicates a closest proximity to the tracked object 10. As described in operation 360, the extremum-reading sensor set 222 may be powered. Set_4 is identified as the first adjacent sensor set 224 because Set_4 is directly adjacent to the extremum-reading sensor set 222. In particular, Set_4 is directly proximally adjacent to the extremum-reading sensor set 222. As described in operation 370, the first adjacent sensor set 224 may be powered. The extremum-reading sensor set 222 is the distal sensor set 166, so there is no sensor set 150 distally adjacent to extremum-reading sensor set. As such, there is no second adjacent sensor set 226 to power in operation 380. Set_4 and Set_5 were identified as the first adjacent sensor set 224 and the extremum-reading sensor set 222, respectively, so Set_0, Set_1, Set_2, and Set_3 are identified as additional sensor sets 392. As described in operation 390, the additional sensor sets 392 are put in an OFF power state 220.

An exemplary third state 430 shows a state of the position determining apparatus 100 after proximal movement of the tracked object 10 to position 4 and before the position 228 and power states 220 are updated by repeating method 300.

A fourth exemplary state 440 shows a state of the position determining apparatus 100 after a subsequent performance of the method 300. In particular, Set_4 is identified as the extremum-reading sensor set 222, Set_3 is identified as the first adjacent set 224, Set_5 is identified as second adjacent set 226, and the position output 228 is the position value of 4. The power states 220 are updated such that Set_0, Set_1, and Set_2 have an ON power state 220 and Set_3, Set_4, and Set_5 have an OFF power state 220.

Figure 12:
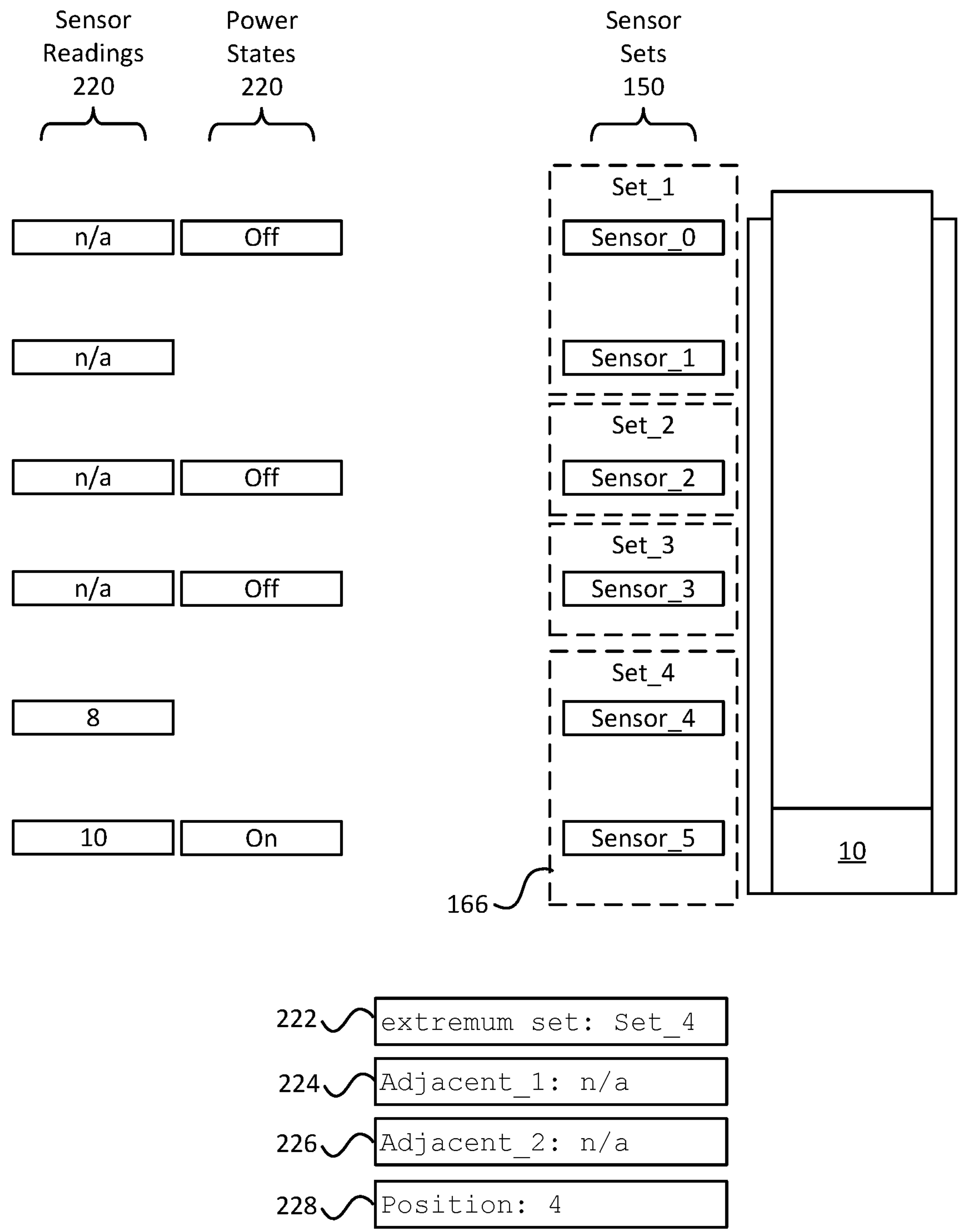
FIG. 12 illustrates an additional power-saving configuration.

FIG. 12 illustrates an alternative power-saving configuration. As illustrated, the adjacency is determined at a position sensor 152 level rather than a sensor set 150 level for the purposes of determining which sensor sets 150 should have what power states 220. For example, position sensors 152 that are adjacent to an extremum-value position sensor 152 may be powered regardless of the sensor set 150 to which the position sensors 152 belong. In the illustrated example, Sensor_5 of Set 4 is an extremum sensor because Sensor_5 is associated with a highest sensor reading (or, other determinative reading) value. The sensor proximally adjacent to Sensor_5 is Sensor_4, which is also part of Set_4. Sensor_5 is a most-distal sensor, so there is no distally-adjacent sensor to Sensor_5. Because all of the adjacent sensors are part of a same sensor set 150, no additional sensor sets 150 are powered. In this arrangement, the position sensors 152 can be considered to be divided into one of two groups: a first group of position sensors that will be powered and a second group of position sensors that will be prevented from being powered. The first group of position sensors includes the extremum-value position sensor 152 and associated adjacent position sensors 152. This use of groups can be in addition to, or instead of, the use of sets described above. For example, after identifying which sensors 152 belong to which group, the controller can cause powering of all sets 150 having sensors 152 in the first group and preventing the powering of all sets 150 having sensors 152 in the second group.

Figure 13:
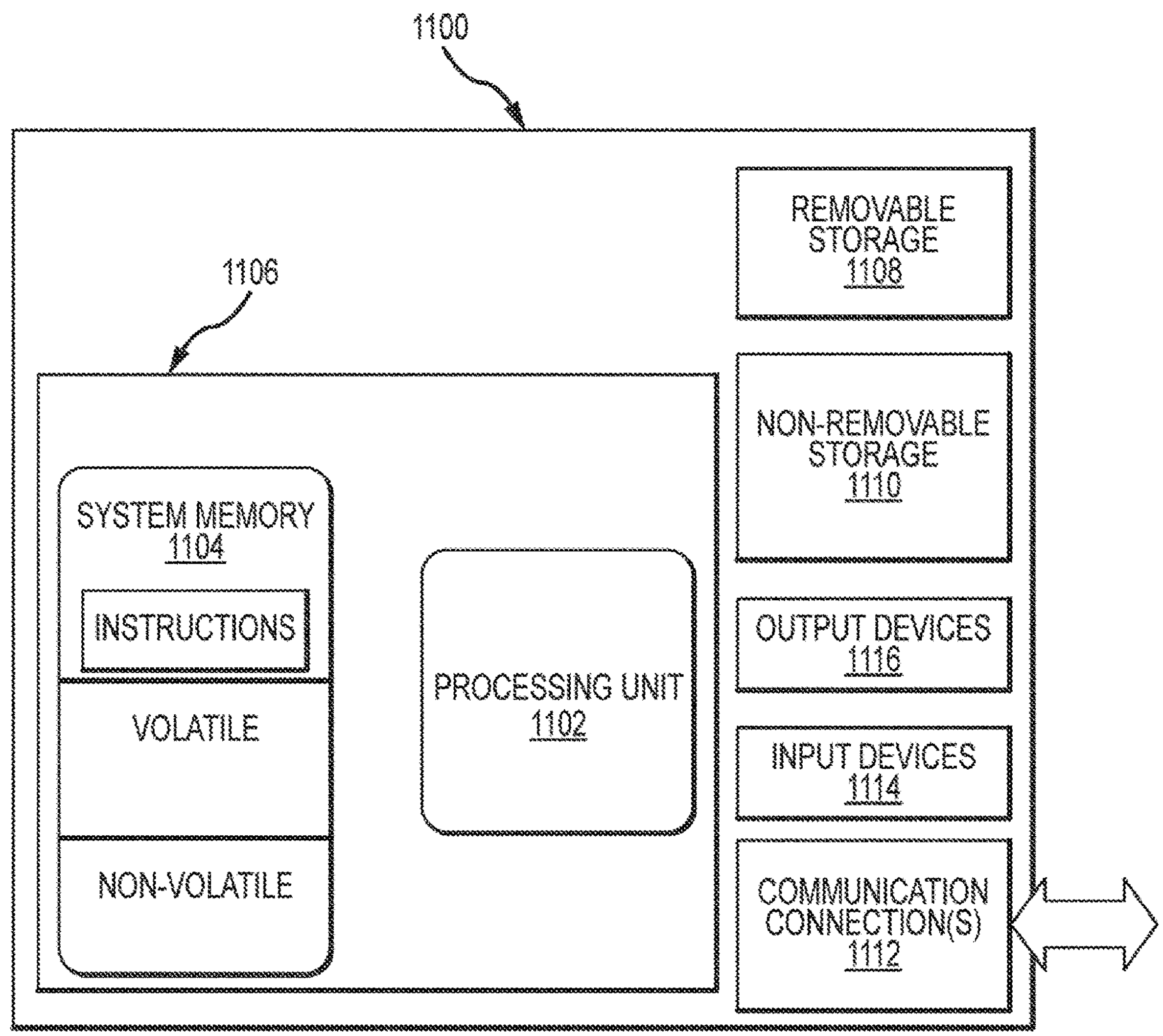
FIG. 13 illustrates one example of a suitable operating environment with which one or more of the present embodiments may be implemented.

FIG. 13 illustrates one example of a suitable operating environment 1100 in which one or more of the present embodiments may be implemented. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 1100 typically includes at least one processing unit 1102 and memory 1104. Depending on the exact configuration and type of computing device, memory 1104 (storing, among other things, instructions to perform the power management methods described herein) may be volatile (such as RAM), non-volatile (such as ROM, flash memory, etc.), or some combination of the two. This most basic configuration is illustrated in FIG. 13 by line 1106. Further, environment 1100 may also include storage devices (removable, 1108, and/or non-removable, 1110) including, but not limited to, magnetic or optical disks or tape. Similarly, environment 1100 may also have input device(s) 1114 such as touch screens, keyboard, mouse, pen, voice input, etc. and/or output device(s) 1116 such as a display, speakers, printer, etc. Also included in the environment may be one or more communication connections, 1112, such as LAN, WAN, point to point, BLUETOOTH, radiofrequency, etc.

Operating environment 1100 typically includes at least some form of computer readable media. Computer readable media can be any available media that can be accessed by processing unit 1102 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1100 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet. In some embodiments, the components described herein comprise such modules or instructions executable by computer system 1100 that may be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 1100 is part of a network that stores data in remote storage media for use by the computer system 1100.

The monitoring syringes such as those described above may be utilized in various types of medium management systems to control and monitor medium injection into patients. Two exemplary medium management systems, as well as components thereof, may be further described in related application U.S. patent application Ser. No. 16/024,768, previously incorporated herein by reference. These are but two types of systems that may benefit from the monitoring technologies described herein. Other systems and configurations thereof will be apparent to a person of skill in the art.

The monitoring systems described herein may be utilized to deliver any types of fluids to a patient during a medical procedure. Such fluids may include medium (media), agents, substances, materials, medicaments, and the like. It should be noted that these terms are used generically herein to describe a variety of fluidal materials that may include, at least in part, a substance used in the performance of a diagnostic, therapeutic or/and prophylactic medical procedure and such use is not intended to be limiting. It should be understood that the medium delivery modulation and/or measurement devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain.

The materials utilized in the manufacture of the monitoring syringe may be those typical in medical applications. Plastics such as polycarbonate may be utilized for the syringe housing and plunger. The band or gradation may be printed directly on the plunger shaft, or may be printed on a discrete plastic sheet or sheath that may then be affixed to the plunger shaft. Various types of printing may be utilized to change the translucency or opacity of the band or gradation. In some embodiments, the type of printing may be based on the type of light to be received by the sensors. For example, carbon-based printing may be utilized for sensors that detect infrared light. Thus, the band or gradation may be utilized as the filter described above.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

What is claimed is:

1. A method comprising:

receiving sensor readings from a plurality of plunger position sensor sets relating to a proximity of a tracked object, wherein each of the plurality of plunger position sensor sets includes one or more plunger position sensors;

identifying an extremum sensor reading from the sensor readings, the extremum sensor reading indicating the tracked object is nearest to an extremum-reading sensor set of the plurality of plunger position sensor sets that corresponds to the extremum sensor reading; and based on the sensor readings:

powering, from a power source, the extremum-reading sensor set;

powering, from the power source, a first adjacent sensor set, wherein the first adjacent sensor set is a sensor set of the plurality of plunger position sensor sets that is adjacent to the extremum-reading sensor set; and preventing one or more additional sensor sets from receiving power from the power source.

2. The method of claim 1, further comprising:

powering a second adjacent sensor set that is adjacent to the extremum-reading sensor set, wherein the one or more additional sensor sets do not include the second adjacent sensor set.

3. The method of claim 2, wherein the first adjacent sensor set is distal to the extremum-reading sensor set; and wherein the second adjacent sensor set is proximal to the extremum-reading sensor set.

4. The method of claim 1, wherein each of the plurality of plunger position sensor sets comprises a Hall Effect sensor, a light sensor, an inductive sensor, or a capacitive touch sensor.

5. The method of claim 1, wherein the one or more additional sensor sets include all plunger position sensor sets other than the first adjacent sensor set and the extremum-reading sensor set.

6. The method of claim 2, wherein the one or more additional sensor sets include all plunger position sensor sets other than the first adjacent sensor set, the second adjacent sensor set, and the extremum-reading sensor set.

7. The method of claim 1, further comprising:

providing a position output corresponding to a position of the tracked object using the sensor readings.

8. The method of claim 7, wherein the tracked object is a plunger of a syringe.

9. The method of claim 1, further comprising:

during an initialization process, powering each plunger position sensor set of the plurality of plunger position sensor sets.

10. The method of claim 1, further comprising:

responsive to the extremum sensor reading failing to satisfy a threshold, powering all plunger position sensor sets of the plurality of plunger position sensor sets.

11. An apparatus comprising:

a syringe housing;

a magnet fixed proximate the syringe housing;

a plunger slidably received within the syringe housing between a first position and a second position, wherein the plunger comprises:

a plurality of plunger position sensor sets comprising:

a distal plunger position sensor set comprising one or more distal plunger position sensors disposed proximate a distal end of the plunger;

a proximal plunger position sensor set comprising one or more proximal plunger position sensors disposed proximate a proximal end of the plunger; and two or more intermediate plunger position sensor sets each comprising one or more intermediate plunger position sensors disposed at a location between the distal plunger position sensor set and the proximal plunger position sensor set;

a power source; and a controller configured to selectively and individually control a power state of each respective plunger position sensor set of the plurality of plunger position sensor sets from the power source based on a sensor reading from each of the plurality of plunger position sensor sets.

12. The apparatus of claim 11, wherein the distal plunger position sensor set comprises a plurality of distal plunger position sensors; and wherein the controller is further configured to selectively control a power state of the plurality of distal plunger position sensors at an entire-set level.

13. The apparatus of claim 11, wherein the plunger further comprises a shift register circuit electrically coupled to the power source, the one or more distal plunger position sensors, the one or more proximal plunger position sensors, and the one or more intermediate plunger position sensors, wherein the shift register circuit is configured to control the power state of the one or more distal plunger position sensors, the one or more proximal plunger position sensors, and the one or more intermediate plunger position sensors based on a signal received from the controller, and wherein the controller is configured to selectively control the power state of each respective plunger position sensor set of the plurality of plunger position sensor sets from the power source at least in part by:

communicating a data signal to the shift register circuit.

14. The apparatus of claim 11, wherein the one or more distal plunger position sensors comprise a Hall Effect sensor, a light sensor, an inductive sensor, or a capacitive touch sensor.

15. A position determining apparatus comprising:

a power source;

a plurality of position sensors, each position sensor of the plurality of position sensors being selectively powered by the power source and configured to provide respective sensor readings indicating a proximity of a tracked object; and a controller configured to:

receive the respective sensor readings of the plurality of position sensors;

identify a position sensor of the plurality of position sensors that provided an extremum sensor reading as being an extremum-value position sensor;

based on the respective sensor readings, cause powering of a first group of the plurality of position sensors and prevent powering of a second group of the plurality of position sensors; and provide a position output based on the respective sensor readings of the first group, wherein the first group includes the extremum-value position sensor.

16. The positioning determining apparatus of claim 15, wherein the first group further includes a first adjacent position sensor adjacent the extremum-value position sensor.

17. The positioning determining apparatus of claim 16, wherein the first group further includes a second adjacent position sensor adjacent the extremum-value position sensor.

18. The positioning determining apparatus of claim 15, wherein the power source is an alkaline battery.

19. The positioning determining apparatus of claim 15, further comprising:

a shift register circuit electrically coupled to the power source, the controller, and the plurality of position sensors, wherein the controller is further configured to cause and prevent the powering by providing a data signal to the shift register circuit.

* * * * *